US010898563B2

(12) United States Patent
Clark

(10) Patent No.: US 10,898,563 B2
(45) Date of Patent: Jan. 26, 2021

(54) CANCER IMMUNE-BASED THERAPY

(71) Applicant: Gary Clark, Columbia, MO (US)

(72) Inventor: Gary Clark, Columbia, MO (US)

(73) Assignee: The Curators of the University of Missouri, Columbia, MO (US)

( * ) Notice: Subject to any disclaimer, the term of this patent is extended or adjusted under 35 U.S.C. 154(b) by 101 days.

(21) Appl. No.: 15/445,576

(22) Filed: Feb. 28, 2017

(65) Prior Publication Data

US 2017/0246275 A1 Aug. 31, 2017

Related U.S. Application Data

(60) Provisional application No. 62/301,298, filed on Feb. 29, 2016.

(51) Int. Cl.
*A61K 39/00* (2006.01)
*C12N 5/09* (2010.01)
*A61K 45/06* (2006.01)
*A61K 9/00* (2006.01)

(52) U.S. Cl.
CPC .. *A61K 39/001169* (2018.08); *A61K 39/0011* (2013.01); *A61K 45/06* (2013.01); *C12N 5/0693* (2013.01); *A61K 9/0021* (2013.01); *A61K 2039/54* (2013.01); *A61K 2039/55505* (2013.01); *A61K 2039/55572* (2013.01)

(58) Field of Classification Search
CPC ...... C12N 5/0693; C12N 9/24; C12N 9/2405; C12N 9/2408; C12N 9/2411; C12N 9/2414; C12N 9/242; C12N 9/2422; C12N 9/2445; C12N 9/2448; C12N 9/2451; C12N 9/2454; C12N 9/2457; C12N 9/246; C12N 9/2462; C12N 9/2465; C12N 9/2468; C12N 9/2471; C12N 9/2474; C12N 9/2477; C12N 9/2402; C12N 9/248; C12N 9/2482; C12N 9/2485; C12N 9/2488; C12N 9/2491; C12N 9/2494; C12N 9/2497; A61P 35/00; A61K 39/001169; A61K 39/0011; A61K 45/06
See application file for complete search history.

(56) References Cited

U.S. PATENT DOCUMENTS

| 7,098,195 | B2* | 8/2006 | Sackstein | A61K 31/137 435/7.24 |
| 2002/0176845 | A1* | 11/2002 | Falkenberg | A61K 39/0011 424/85.1 |
| 2009/0214585 | A1* | 8/2009 | Ciocca | A61K 39/0011 424/193.1 |
| 2015/0191695 | A1* | 7/2015 | Song | C12N 5/0639 424/277.1 |

FOREIGN PATENT DOCUMENTS

| WO | WO-9834641 A1 * | 8/1998 | ......... A61K 39/0011 |
| WO | WO-2006110172 A2 * | 10/2006 | ............. A61K 31/56 |

OTHER PUBLICATIONS

Agard and Bertozzi, Accounts of Chemical Research, 2009, vol. 42, pp. 788-797 (Year: 2009).*
Bielinska et al (Journal of Biological Chemistry, 1978, vol. 20, pp. 7117-7119) (Year: 1978).*
Sedlacek et al (Klinische Wochen-Schrift, 1977, vol. 55, pp. 199-214 (Year: 1977).*
Sedlacek et al (International Journal of Immunopharmacology, 1987, vol. 9, pp. 841-850 (Year: 1987).*
Supporting information for Xiao et al (Proceedings of the National Academy of Science, 2016, vol. 113) (Year: 2016).*
Kozbor (Immunology Research, 2010, vol. 46, pp. 23-31) (Year: 2010).*
Didierlaurent et al (Journal of Immunology, 2009, vol. 183, pp. 6186-6197) (Year: 2009).*
Gajewski (Seminars in Oncology, 2015, vol. 42, pp. 663-671) (Year: 2015).*
Gerken et al (Biochemistry, 1992, vol. 31, pp. 639-648) (Year: 1992).*

* cited by examiner

*Primary Examiner* — Karen A. Canella
(74) *Attorney, Agent, or Firm* — Tracey S. Truitt; Armstrong Teasdale LLP

(57) ABSTRACT

The present disclosure provides a novel therapeutic vaccine approach that triggers a therapeutic antitumor response. The inventive approach is to selectively eliminate the carbohydrate sequences from tumor cells without affecting the tumor associated protein epitopes.

25 Claims, 3 Drawing Sheets

CANCER IMMUNE-BASED THERAPY

FIELD

The present disclosure relates to cancer therapy, more particularly to a therapeutic vaccine that triggers a therapeutic antitumor response.

BACKGROUND

The statements in this section merely provide background information related to the present disclosure and may not constitute prior art.

Cancer is an abnormal proliferation of cells, and in many cases their dissemination, that can occur virtually anywhere in any multicellular organism (1). In 2016, there were estimated to be 1,685,210 new cases of human cancer diagnosed in the United States, excluding in situ, squamous and basal cell type carcinomas (2). The corresponding estimated number of deaths due to cancer was 595,690. According to the latest available figures, 42% of human males and 38% of all females will eventually develop cancer during their lifetime (2). The same statistical data indicate that 22.6% of men and 19.1% of females will eventually succumb to cancer (2). Classical immunization strategies have failed to block the development of metastatic cancer, and in some cases tend to actually decrease survival (3). All therapeutic cancer vaccines, with one possible exception (Provenge, sipuleucel-T) have not had any positive effect on survival (4).

Statistical data confirm that the majority of humans and companion animals do not develop lethal malignant tumors (5-8). How this majority resists the development of cancer has been a subject of debate for many years. In 1967, Nobelist F. M. Burnet proposed that a major function of the immune system is the elimination of tumor cells, a concept that he designated "immune surveillance" (9). According to this model, lymphocytes act as sentinels that recognize specific tumor associated antigens that arise from spontaneous mutations. Tumor associated antigens are also often referred to as neoantigens (10). Neoantigens enable the efficient immune destruction of tumor cells as they emerge due to mutation. According to this model, spontaneous fatal tumors arise because: (i) malignant cells had somehow managed to escape immunosurveillance; or (ii) the immune system was compromised in some way that inhibited antitumor cell responses (9).

The immune surveillance model did not go unchallenged, however. A study in 1976 involving a very large number of mice and 27 different spontaneously arising tumor types suggested that malignant cells are not recognized by the immune system (11). This result led many cancer investigators to incorrectly conclude that the major problem with tumor cells was aberrant proliferation rather than immune evasion. However, reports published in the 1990s confirmed that tumor cells are genomically unstable and display many mutations. For example, a single colorectal carcinoma was identified that exhibited over 11,000 genomic alterations, suggesting that malignant cells express abundant neoantigens (12). In addition, mice deficient in specific key immune activating molecules (recombinase-activating gene, STAT, perforin, interferon-γ, and interferon-γ receptor) were also shown to have higher incidences of carcinogen-induced tumors and spontaneous epithelial carcinomas (13). These results were consistent with immunosurveillance that targets tumor cells for destruction, preventing the development of lethal cancers. A plethora of evidence now firmly supports the immune surveillance model for the prevention of cancer (14, 15).

Burnet's model immediately suggested that tumor cell vaccines should be useful for preventing the development of cancer by stimulating the immune system. However, immunization with either syngeneic or allogeneic tumor cell lysates did not prevent the development of spontaneous cancer in either humans or animal models (16, 17). To address this lack of a durable response, vaccinologists suggested that tumor antigens would be more effective if administered as part of a therapeutic rather than a preventative vaccine (18). However, the results with therapeutic vaccines have also been poor (3). Perhaps the most notable case was Canvaxin, a therapeutic human melanoma vaccine that was composed of tumor cell lysates from three allogeneic melanoma cell lines combined with a powerful adjuvant (*Bacillus* Calmette-Guérin; BCG) (19). Surprisingly, this vaccine yielded worse outcomes in treated patients than in controls in a large Phase III clinical trial, actually significantly decreasing survival (3).

How could such counterintuitive results be obtained if tumor cells express many different neoantigens as modern genomic analyses have unequivocally confirmed (20)? These observations suggest that tumor cells in cancer patients must be employing a natural pathway of immune suppression to escape destruction. One natural pathway was implied in the mammalian reproductive system. In 1953, Nobel Laureate Sir Peter Medawar posed the following question: "How does the pregnant mother nourish within itself for many weeks or months a fetus that is antigenically a foreign body?" (21). The mammalian fetus is a foreign body to the mother because of the presence of paternal major histocompatibility complex (MHC) molecules. The fetus is completely foreign if development occurs in the uterus of an unrelated surrogate mother facilitated by human IVF. How female placental mammals (eutherians) can accommodate the foreign fetus has been a major question since this enigma was proposed over sixty years ago (22-27).

Other studies in the field of reproductive immunology have revealed other immunological enigmas that are likely applicable to all placental mammals (eutherians). A good example is the observation that human sperm and eggs completely lack major histocompatibility complex (MHC) molecules known as human leukocyte antigens (HLA) (28). Because of the absence of HLA, human gametes cannot trigger allogeneic immune responses, nor are they sensitive to such responses. On the other hand, natural killer (NK) cells express specific inhibitory receptors that bind to HLA class I molecules on potential target cells. Engagement of these receptors promotes tolerance of somatic cells expressing these HLA class I molecules (29). Since human sperm and eggs lack HLA molecules, how these gametes evade NK cell responses represents another major immunological enigma.

Human sperm pose yet another major immunological enigma. Spermatogenesis is initiated in human males during puberty, long after the period of thymic education (30). Sperm proteins are specifically expressed for the first time during the onset of puberty, suggesting that they are antigenic. Such proteins are often referred to as either autoantigens or neoantigens (31, 32). Several tolerizing factors are expressed in the human male urogenital tract and seminal plasma that likely block immune responses directed against sperm autoantigens (33). However, human seminal plasma factors do not enter the uterus, but sperm have complete access to the female urogenital tract. How human sperm block adaptive immune responses directed against their neoantigens in females is yet another major immunological enigma.

The human fetoembryonic defense system (Hu-FEDS) hypothesis was initially proposed in 1996 to address these major immunological enigmas in reproduction. In this model, a specific glycoprotein designated glycodelin-A (GdA) and mucins present in the placenta, amniotic fluid and decidua were implicated as factors that suppress the maternal immune response in the pregnant uterus. These glycoconjugates were suggested to manifest their effects by employing their glycans as carbohydrate functional groups (CFGs) to block immune cell binding or interact with lectin-like receptors coupled to signal transduction proteins that modulate immune responses (34).

A pathway for the protection of HLA class I negative human sperm from NK cell was proposed in 1996 as a component of the Hu-FEDS model. HLA class I negative K562 erythroleukemia cells are efficiently lysed in NK cell cytotoxicity assays (35). However, K562 cells become completely resistant to NK cell lysis if the level of expression of a specific carbohydrate sequence known as the biantennary bisecting type (BBSCT) N-glycan is elevated on their surface (36, 37). Subsequent sequencing of the N-glycans expressed on human sperm glycoproteins combined with the binding of a lectin specific for bisecting type N-glycan (erythroagglutinating phytohemagglutinin; E-PHA) confirmed that BBSCT N-glycans are profusely expressed on the plasma membrane of human sperm (38, 39). These results are consistent with the concept that human sperm evade NK cell responses by expressing BBSCT N-glycans.

Data has also become available to explain how HLA class I negative human eggs evade NK cell lysis. There is evidence that two different types of carbohydrate sequences are protective. The outer specialized matrix of the egg known as the zona pellucida is coated with sialyl-Lewis$^x$ sequences (SLEX) (38). SLEX is a ligand for Siglec-9, a lectin-like inhibitory receptor on NK cells that bears an immunoreceptor tyrosine-based inhibitory motif (ITIM) (40). The plasma membrane of the human egg cell also stains intensely with E-PHA, indicating that glycoproteins bearing BBSCT N-glycans are likely also expressed on the surface of these germ cells.

Specific CFGs associated with human sperm could also play a role in evoking tolerance to neoantigens associated with this cell type in the female reproductive system. Glycomic analysis of human sperm indicates that many of their glycoproteins bear terminal Lewis$^y$ sequences (41). These carbohydrate sequences are ligands for another immune lectin (DC-SIGN) that is expressed on the surface of dendritic cells (42). The binding of glycans bearing fucosylated ligands like Lewis$^y$ to DC-SIGN inhibits the development of adaptive immune responses by dendritic cells (43).

A major question is how do tumor cells circumvent immune surveillance in cancer victims? Thirty years ago, murine monoclonal antibodies (mAb) were obtained that specifically reacted with human tumor cells but not their progenitor cells. One mAb (AH-6) was bound to Lewis$^y$ while the other mAb (CSLEX) was bound to SLEX (44, 45). Lewis$^y$ and SLEX were therefore initially referred to as tumor associated carbohydrate antigens (TACAs) long before any other function was ascribed to them. About 70-80% of all human tumor cells of epithelial origin (adenocarcinomas) substantially increase the expression of SLEX and Lewis$^y$ on their surfaces (44-46). SLEX and Lewis$^y$ sequences are attached to all three major classes of glycoconjugates on human tumor cells (N-glycans, O-glycans, glycosphingolipids) (44, 47, 48). The Lewis$^y$ sequence was previously shown to be a useful target in antibody-directed radioimmunotherapy in dogs (49). BBSCT N-glycan expression is also often elevated on the surface of tumor cells arising from different organs (50)

Other major human TACAs include glycosphingolipids (globo H, GM2, GD2, GD3) and antigens attached to N-glycans, O-glycans or glycosphingolipids (H blood group, Lewis$^a$, sialyl-Lewis$^a$, Tn, sialyl-Tn) (47). Compared to human melanocytes, melanoma cells overexpress gangliosides GM2, GD2, and GD3 (51). GD3 is a ligand for Siglec-7, another ITIM type receptor on NK cells that inhibits lytic responses (52). Metastatic human melanoma cells also present high levels of linear polylactosamine type sequences on their N-glycans that are undetectable in normal melanocytes (53). Similarly, elevated levels of polylactosamines are also observed on invasive colorectal, pancreatic, breast, lung, hepatocellular, ovarian and papillary cancer, but not their progenitor cells. Linear polylactosamine sequences bind specifically to galectins. Galectins have been shown to induce substantial modulatory effects on the human immune response (54, 55).

As noted earlier, glycodelin-A is a glycoprotein with substantial immune modulatory activity that is expressed in the pregnant human uterus (56). A specific CFG that has been implicated in mediating its biological activity is the fucosylated lacdiNAc sequence (57). Recent analyses indicate that this sequence is highly expressed on poorly differentiated human colorectal cancer cells with high metastatic potential (48). In summary, many and perhaps all of the CFGs that protect human gametes and the developing eutherian in utero from the maternal immune response are also being deployed by mammalian tumor cells to protect them from immune surveillance (58).

Much less is known about the glycosylation of canine and feline tumor cells than human tumor cells. Nonetheless, there is evidence that SLEX expression is upregulated on about 70% of all canine and feline mammary gland tumors (59-61). Similarly, Lewis$^y$ is expressed on 52% of the carcinomas of mammary, prostatic, bronchogenic, nasal, hepatic, rectal, tonsillar squamous, lacrimal gland, and nasal planum squamous origin (62). A substantial increase in the expression of T and Tn antigens were also observed on canine mammary tubulopapillary carcinomas as compared to simple benign adenomas in dogs (63). In summary, there are indications that, like human tumor cells, similar carbohydrate sequences are being expressed during oncogenic development in dogs and cats. It is likely that they are also being used in a similar fashion to protect canine and feline-tumor cells from destruction.

Major shifts in the glycosylation of tumor cells constitute a specific hallmark of cancer (64). Substantial data indicate that tumor cells begin to express the same CFGs that are employed to protect the gametes and the developing fetus in utero. The evidence indicates that this pattern of altered glycoconjugate expression acts as a "glycan shield" that protects aggressive tumor cells from the adaptive immune response. In essence, this shield enables these tumor cells to couple their survival to the reproductive imperative. This glycan shield likely exists in all eutherians, and in lower species in the form of protection for gametes (56). By specifically attacking this shield, we enable immune effector cells to detect the tumor neoantigens. It is very likely that once immune cells can clearly "see" these neoantigens, they lose their ability to be inhibited by these CFGs, and attack the tumor cells, leading to their lysis and the destruction of solid tumors. Our data clearly supports this strategy as a viable immunotherapy for mammalian cancer.

Therefore, there is a need to provide an antitumor therapy to disrupt the glycan shielding on the tumor cells of humans and/or companion animals to activate the immune response against the tumor cells.

The teaching and content of the following references is hereby incorporated by references herein.

1. Hernandez-Divers, S. M., and Garner, M. M. (2003) Neoplasia of reptiles with an emphasis on lizards. *Vet Clin North Am Exot Anim Pract* 6, 251-273
2. Society, A. C. (2016) Cancer Facts and Figures 2016. American Cancer Society, found on the web at cancer.org
3. Goldman, B., and DeFrancesco, L. (2009) The cancer vaccine roller coaster. *Nature biotechnology* 27, 129-139
4. Cheever, M. A., and Higano, C. S. (2011) PROVENGE (Sipuleucel-T) in prostate cancer: the first FDA-approved therapeutic cancer vaccine. *Clinical cancer research: an official journal of the American Association for Cancer Research* 17, 3520-3526
5. ACS (2013) Cancer Facts and Figures. American Cancer Society
6. Bronson, R. T. (1982) Variation in age at death of dogs of different sexes and breeds. *American journal of veterinary research* 43, 2057-2059
7. Adams, V. J., Evans, K. M., Sampson, J., and Wood, J. L. (2010) Methods and mortality results of a health survey of purebred dogs in the UK. *J Small Anim Pract* 51, 512-524
8. Blackwood, L. (2013) Cats with cancer: where to start. *J Feline Med Surg* 15, 366-377
9. Burnet, M. (1957) Cancer; a biological approach. I. The processes of control. *Br Med J* 1, 779-786
10. Huebner, R. J., Casey, M. J., Chanock, R. M., and Schell, K. (1965) Tumors induced in hamsters by a strain of adenovirus type 3: sharing of tumor antigens and "neoantigens" with those produced by adenovirus type 7 tumors. *Proceedings of the National Academy of Sciences of the United States of America* 54, 381-388
11. Hewitt, H. B., Blake, E. R., and Walder, A. S. (1976) A critique of the evidence for active host defence against cancer, based on personal studies of 27 murine tumours of spontaneous origin. *British journal of cancer* 33, 241-259
12. Stoler, D. L., Chen, N., Basik, M., Kahlenberg, M. S., Rodriguez-Bigas, M. A., Petrelli, N. J., and Anderson, G. R. (1999) The onset and extent of genomic instability in sporadic colorectal tumor progression. *Proceedings of the National Academy of Sciences of the United States of America* 96, 15121-15126
13. Schreiber, R. D., Old, L. J., and Smyth, M. J. (2011) Cancer immunoediting: integrating immunity's roles in cancer suppression and promotion. *Science* 331, 1565-1570
14. Marcus, A., Gowen, B. G., Thompson, T. W., Iannello, A., Ardolino, M., Deng, W., Wang, L., Shifrin, N., and Raulet, D. H. (2014) Recognition of tumors by the innate immune system and natural killer cells. *Advances in immunology* 122, 91-128
15. Gross, E., Sunwoo, J. B., and Bui, J. D. (2013) Cancer immunosurveillance and immunoediting by natural killer cells. *Cancer J* 19, 483-489
16. Stewart, T. H., and Orizaga, M. (1971) The presence of delayed hypersensitivity reactions in patients toward cellular extracts of their malignant tumors. 3. The frequency, duration, and cross reactivity of this phenomenon in patients with breast cancer, and its correlation with survival. *Cancer* 28, 1472-1478
17. LaSalle, B. (1968) Veterinary vaccines. *Natl Cancer Inst Monogr* 29, 515-522
18. Curigliano, G., Spitaleri, G., Pietri, E., Rescigno, M., de Braud, F., Cardillo, A., Munzone, E., Rocca, A., Bonizzi, G., Brichard, V., Orlando, L., and Goldhirsch, A. (2006) Breast cancer vaccines: a clinical reality or fairy tale? *Ann Oncol* 17, 750-762
19. Morton, D. L., Hsueh, E. C., Essner, R., Foshag, L. J., O'Day, S. J., Bilchik, A., Gupta, R. K., Hoon, D. S., Ravindranath, M., Nizze, J. A., Gammon, G., Wanek, L. A., Wang, H. J., and Elashoff, R. M. (2002) Prolonged survival of patients receiving active immunotherapy with Canvaxin therapeutic polyvalent vaccine after complete resection of melanoma metastatic to regional lymph nodes. *Annals of surgery* 236, 438-448; discussion 448-439
20. Alexandrov, L. B., Nik-Zainal, S., Wedge, D. C., Aparicio, S. A., Behjati, S., Biankin, A. V., Bignell, G. R., Bolli, N., Borg, A., Borresen-Dale, A. L., Boyault, S., Burkhardt, B., Butler, A. P., Caldas, C., Davies, H. R., Desmedt, C., Eils, R., Eyfjord, J. E., Foekens, J. A., Greaves, M., Hosoda, F., Hutter, B., Ilicic, T., Imbeaud, S., Imielinski, M., Jager, N., Jones, D. T., Jones, D., Knappskog, S., Kool, M., Lakhani, S. R., Lopez-Otin, C., Martin, S., Munshi, N. C., Nakamura, H., Northcott, P. A., Pajic, M., Papaemmanuil, E., Paradiso, A., Pearson, J. V., Puente, X. S., Raine, K., Ramakrishna, M., Richardson, A. L., Richter, J., Rosenstiel, P., Schlesner, M., Schumacher, T. N., Span, P. N., Teague, J. W., Totoki, Y., Tutt, A. N., Valdes-Mas, R., van Buuren, M. M., van 't Veer, L., Vincent-Salomon, A., Waddell, N., Yates, L. R., Australian Pancreatic Cancer Genome, I., Consortium, I. B. C., Consortium, I. M.-S., PedBrain, I., Zucman-Rossi, J., Futreal, P. A., McDermott, U., Lichter, P., Meyerson, M., Grimmond, S. M., Siebert, R., Campo, E., Shibata, T., Pfister, S. M., Campbell, P. J., and Stratton, M. R. (2013) Signatures of mutational processes in human cancer. *Nature* 500, 415-421
21. Medawar, P. (1953) Some immunological and endocrinological problems raised by the evolution of viviparity in vertebrates. *Symp. Soc. Exp. Biol. VII,* 320-338
22. PrabhuDas, M., Bonney, E., Caron, K., Dey, S., Erlebacher, A., Fazleabas, A., Fisher, S., Golos, T., Matzuk, M., McCune, J. M., Mor, G., Schulz, L., Soares, M., Spencer, T., Strominger, J., Way, S. S., and Yoshinaga, K. (2015) Immune mechanisms at the maternal-fetal interface: perspectives and challenges. *Nature immunology* 16, 328-334
23. Moffett, A., and Loke, C. (2006) Immunology of placentation in eutherian mammals. *Nature reviews. Immunology* 6, 584-594
24. Trowsdale, J., and Betz, A. G. (2006) Mother's little helpers: mechanisms of maternal-fetal tolerance. *Nature immunology* 7, 241-246
25. Prins, J. R., Gomez-Lopez, N., and Robertson, S. A. (2012) Interleukin-6 in pregnancy and gestational disorders. *Journal of reproductive immunology* 95, 1-14
26. Arck, P. C., and Hecher, K. (2013) Fetomaternal immune cross-talk and its consequences for maternal and offspring's health. *Nature medicine* 19, 548-556
27. Erlebacher, A. (2013) Mechanisms of T cell tolerance towards the allogeneic fetus. *Nature reviews. Immunology* 13, 23-33
28. Hutter, H., and Dohr, G. (1998) HLA expression on immature and mature human germ cells. *Journal of reproductive immunology* 38, 101-122

29. Long, E. O., Kim, H. S., Liu, D., Peterson, M. E., and Rajagopalan, S. (2013) Controlling natural killer cell responses: integration of signals for activation and inhibition. *Annual review of immunology* 31, 227-258

30. Kourilsky, P., and Claverie, J. M. (1989) MHC restriction, alloreactivity, and thymic education: a common link? *Cell* 56, 327-329

31. Tung, K. S., Teuscher, C., and Meng, A. L. (1981) Autoimmunity to spermatozoa and the testis. *Immunological reviews* 55, 217-255

32. Tung, K. S., Fusi, F., and Teuscher, C. (2002) Autoimmune disease of the spermatozoa, ovary and testis. In: N., T. A., and Bona, C., eds. *The Molecular Pathology of Autoimmune Diseases*, pp. 1031-1045, Routledge Publishers 33. Clark, G. F., and Schust, D. J. (2013) Manifestations of immune tolerance in the human female reproductive tract. *Frontiers in immunology* 4, 26

34. Clark, G. F., Oehninger, S., Patankar, M. S., Koistinen, R., Dell, A., Morris, H. R., Koistinen, H., and Seppala, M. (1996) A role for glycoconjugates in human development: the human fetoembryonic defence system hypothesis. *Human reproduction* 11, 467-473

35. Kay, H. D., Fagnani, R., and Bonnard, G. D. (1979) Cytotoxicity against the K562 erythroleukemia cell line by human natural killer (NK) cells which do not bear free Fc receptors for IgG. *International journal of cancer. Journal international du cancer* 24, 141-150

36. el Ouagari, K., Teissie, J., and Benoist, H. (1995) Glycophorin A protects K562 cells from natural killer cell attack. Role of oligosaccharides. *The Journal of biological chemistry* 270, 26970-26975

37. Yoshimura, M., Ihara, Y., Ohnishi, A., Ijuhin, N., Nishiura, T., Kanakura, Y., Matsuzawa, Y., and Taniguchi, N. (1996) Bisecting N-acetylglucosamine on K562 cells suppresses natural killer cytotoxicity and promotes spleen colonization. *Cancer research* 56, 412-418

38. Pang, P. C., Chiu, P. C., Lee, C. L., Chang, L. Y., Panico, M., Morris, H. R., Haslam, S. M., Khoo, K. H., Clark, G. F., Yeung, W. S., and Dell, A. (2011) Human sperm binding is mediated by the sialyl-Lewis$^x$ oligosaccharide on the zona pellucida. *Science* 333, 1761-1764

39. Patankar, M. S., Ozgur, K., Oehninger, S., Dell, A., Morris, H., Seppala, M., and Clark, G. F. (1997) Expression of glycans linked to natural killer cell inhibition on the human zona pellucida. *Molecular human reproduction* 3, 501-505

40. Angata, T., and Varki, A. (2000) Cloning, characterization, and phylogenetic analysis of siglec-9, a new member of the CD33-related group of siglecs. Evidence for co-evolution with sialic acid synthesis pathways. *The Journal of biological chemistry* 275, 22127-22135

41. Pang, P. C., Tissot, B., Drobnis, E. Z., Sutovsky, P., Morris, H. R., Clark, G. F., and Dell, A. (2007) Expression of bisecting type and Lewisx/Lewisy terminated N-glycans on human sperm. *The Journal of biological chemistry* 282, 36593-36602

42. Garcia-Vallejo, J. J., and van Kooyk, Y. (2013) The physiological role of DC-SIGN: a tale of mice and men. *Trends in immunology* 34, 482-486

43. Gringhuis, S. I., den Dunnen, J., Litjens, M., van der Vlist, M., and Geijtenbeek, T. B. (2009) Carbohydrate-specific signaling through the DC-SIGN signalosome tailors immunity to *Mycobacterium tuberculosis*, HIV-1 and *Helicobacter pylori*. *Nature immunology* 10, 1081-1088

44. Fukushima, K., Hirota, M., Terasaki, P. I., Wakisaka, A., Togashi, H., Chia, D., Suyama, N., Fukushi, Y., Nudelman, E., and Hakomori, S. (1984) Characterization of sialosylated Lewis$^x$ as a new tumor-associated antigen. *Cancer research* 44, 5279-5285

45. Abe, K., McKibbin, J. M., and Hakomori, S. (1983) The monoclonal antibody directed to difucosylated type 2 chain (Fuca1-2Galb1-4[Fuca1-3]GlcNAc; Y Determinant). *The Journal of biological chemistry* 258, 11793-11797

46. Hellstrom, I., Garrigues, H. J., Garrigues, U., and Hellstrom, K. E. (1990) Highly tumor-reactive, internalizing, mouse monoclonal antibodies to Le(y)-related cell surface antigens. *Cancer research* 50, 2183-2190

47. Hakomori, S. (2001) Tumor-associated carbohydrate antigens defining tumor malignancy: basis for development of anti-cancer vaccines. *Advances in experimental medicine and biology* 491, 369-402

48. Sethi, M. K., Thaysen-Andersen, M., Smith, J. T., Baker, M. S., Packer, N. H., Hancock, W. S., and Fanayan, S. (2014) Comparative N-glycan profiling of colorectal cancer cell lines reveals unique bisecting GlcNAc and alpha-2,3-linked sialic acid determinants are associated with membrane proteins of the more metastatic/aggressive cell lines. *Journal of proteome research* 13, 277-288

49. Bryan, J. N., Jia, F., Mohsin, H., Sivaguru, G., Anderson, C. J., Miller, W. H., Henry, C. J., and Lewis, M. R. (2011) Monoclonal antibodies for copper-64 PET dosimetry and radio immunotherapy. *Cancer Biol Ther* 11, 1001-1007

50. Christiansen, M. N., Chik, J., Lee, L., Anugraham, M., Abrahams, J. L., and Packer, N. H. (2013) Cell surface protein glycosylation in cancer. *Proteomics*

51. Hakomori, S. (1984) Tumor-associated carbohydrate antigens. *Annual review of immunology* 2, 103-126

52. Nicoll, G., Avril, T., Lock, K., Furukawa, K., Bovin, N., and Crocker, P. R. (2003) Ganglio side GD3 expression on target cells can modulate NK cell cytotoxicity via siglec-7-dependent and -independent mechanisms. *European journal of immunology* 33, 1642-1648

53. Kinoshita, M., Mitsui, Y., Kakoi, N., Yamada, K., Hayakawa, T., and Kakehi, K. (2014) Common glycoproteins expressing polylactosamine-type glycans on matched patient primary and metastatic melanoma cells show different glycan profiles. *Journal of proteome research* 13, 1021-1033

54. Ruvolo, P. P. (2016) Galectin-3 as a guardian of the tumor microenvironment. *Biochimica et Biophysica Acta* 1863, 427-433

55. Boligan, K. F., Mesa, C., Fernandez, L. E., and von Gunten, S. (2015) Cancer intelligence acquired (CIA): tumor glycosylation and sialylation codes dismantling antitumor defense. *Cellular and Molecular Life Sciences* 72, 1231-1248.

56. Dell, A., Morris, H. R., Easton, R. L., Panico, M., Patankar, M., Oehninger, S., Koistinen, R., Koistinen, H., Seppala, M., and Clark, G. F. (1995) Structural analysis of the oligosaccharides derived from glycodelin, a human glycoprotein with potent immunosuppressive and contraceptive activities. *The Journal of biological chemistry* 270, 24116-24126.

57. Clark, G. F., Dell, A., Morris, H. R., Patankar, M., Oehninger, S., and Seppala, M. (1997) Viewing AIDS from a glycobiological perspective: potential linkages to the human fetoembryonic defence system hypothesis. *Molecular human reproduction* 3, 5-13

58. Clark, G. F. (2014) The role of glycans in immune evasion: the human fetoembryonic defence system hypothesis revisited. *Molecular human reproduction* 20, 185-199
59. Janke, L., Carlson, C. S., and St Hill, C. A. (2010) The novel carbohydrate tumor antigen C2-O-sLe x is upregulated in canine gastric carcinomas. *Veterinary pathology* 47, 455-461
60. Nakagawa, T., Uyama, R., Ohashi, E., Takahashi, T., Hong, S. H., Mochizuki, M., Matsunaga, S., Nishimura, R., and Sasaki, N. (2002) The expression of sialyl Lewis X in canine and feline mammary gland tumors. *The Journal of veterinary medical science/the Japanese Society of Veterinary Science* 64, 949-952
61. Pinho, S. S., Matos, A. J., Lopes, C., Marcos, N. T., Carvalheira, J., Reis, C. A., and Gartner, F. (2007) Sialyl Lewis x expression in canine malignant mammary tumours: correlation with clinicopathological features and E-Cadherin expression. *BMC Cancer* 7, 124
62. Henry, C. J., Buss, M. S., Hellstrom, I., Hellstrom, K. E., Brewer, W. G., Bryan, J. N., and Siegall, C. B. (2005) Clinical evaluation of BR96 sFv-PE40 immunotoxin therapy in canine models of spontaneously occurring invasive carcinoma. *Clinical cancer research: an official journal of the American Association for Cancer Research* 11, 751-755
63. Nowak, M., Madej, J., Dziegiel, P., Lopuszynski, W., Rodo, A., and Ugorski, M. (2009) Tumor-associated carbohydrate antigens: Sialyl Lea and T/Tn antigens in canine mammary tumors. *Veterinary pathology* 46, 222-226
64. Vajaria, B. N., and Patel, P. S. (2016) Glycosylation: a hallmark of cancer? *Glycoconjugate journal* (currently epub ahead of print)

SUMMARY

The present disclosure provides a novel therapeutic vaccine approach that triggers a therapeutic antitumor response. More specifically, according to one embodiment of the disclosure, the method may comprise the step of inoculating of a subject (human or other mammal) with autologous deglycosylated tumor cell lysates to evoke an immune-based antitumor response. In some forms, the potency of the lysates is inversely correlated with the stage of the cancer, the age of the subject, the immune status of said subject (the cancer patient), or a combination of these factors.

According to another embodiment of the disclosure, the method may comprise the step of inoculating of a healthy subject (human or other mammal) with syngeneic or HLA class I negative deglycosylated metastatic tumor cell lysates to evoke a durable antitumor response directed against neoantigens to prevent or greatly impede the development of aggressive cancer. This immunization approach may enable all humans and other mammals to resist the development of metastatic cancer for as long as immunocompetence is maintained. Generally speaking, immunocompetence is maintained in the great majority of humans until at least age 80, unless the person is a smoker, engages in excessive alcohol consumption, or suffers from a known genetic or acquired immunodeficiency.

I. Methods (a) Preparing an Adjuvanted, Deglycosylated Autologous Tumor Vaccine and Treatment One embodiment of the present disclosure provides methods of preparing an adjuvanted, deglycosylated autologous tumor vaccine and treatment that may be derived from the tumor cells of a patient. The method comprises harvesting and isolating cancer cells from patient cancers for incubation with one or more deglycosylation agents and/or inhibitors wherein after the incubation a majority of the cancer cell membrane is deglycosylated. As described herein, "deglycosylated" refers to the disruption of glycolytic linkages, inhibition of forming glycolytic linkages, or disruption and inhibition of forming glycolytic linkages on at least a majority of the cancer cell membrane. Deglycosylation disrupts the carbohydrate functional groups (CFGs) and subsequent glycan shielding to expose the neoantigens and thereby permit the immune system to detect and attack cancer cells once the composition is administered to the patient. The method also comprises combining deglycosylated cancer cell lysate with at least one additional component selected from the group consisting of pharmaceutically-acceptable carriers, adjuvants, diluents, preservatives, antibiotics, and combinations thereof. In some forms, the cancer cells are tumor cells and in other forms, the cancer cells are from liquid cancers such as leukemia. It is understood that when "tumor cells" are referenced herein, it also encompasses cells from liquid cancers.

(i) Harvesting Cancerous Tissues and Liquid Cancers for Isolated Cancer Cells

Generally speaking, methods of harvesting cancer cells from patients are known in the art. In certain embodiments, the patient refers to an animal that has presented with cancer. In certain embodiments, the patient may be a mammal, and in some embodiments, the patient may be a human. In certain embodiments, a patient may be a livestock animal (horse, cow, pig, sheep, etc.) or a companion animal (dog, cat, etc.). In a particular embodiment, the patient may be canine.

In one aspect of the present disclosure, the patient may have cancer at any stage of disease progression. In one embodiment, the patient may have Stage I-IV cancer. In another embodiment, the patient has Stage I-III cancer. In another embodiment, the patient has Stage I-II cancer. In another embodiment, the patient has Stage I cancer. In another embodiment, the cancer may be a primary cancer, a metastases, or primary cancer and metastases. In yet another embodiment, the cancer may be a solid cancer. In still another embodiment, the cancer may be a liquid cancer. Non-limiting examples of cancer types include carcinomas, sarcomas, lymphomas, leukemias, myelomas and mixed types (e.g., blastomas).

In one embodiment, cancer cells may be harvested from a solid tumor, a metastatic node or a solid tumor and a metastatic node, or a liquid cancer. In one embodiment, a harvested tumor cell source may be less than about $0.2$ $cm^3$ to at least about $20$ $cm^3$ or greater, at least about $2$ $cm^3$ to at least about $18$ $cm^3$ or greater, at least about $3$ $cm^3$ to at least about $15$ $cm^3$ or greater, at least about $4$ $cm^3$ to at least about $12$ $cm^3$ or greater, at least about $5$ $cm^3$ to at least about $10$ $cm^3$ or greater, or at least about $6$ $cm^3$ to at least about $8$ $cm^3$ or greater. A harvested tumor cell source may be at least about $0.2$ $cm^3$ or greater, at least about $0.3$ $cm^3$ or greater, at least about $0.4$ $cm^3$ or greater, at least about $0.5$ $cm^3$ or greater, at least about $1$ $cm^3$ or greater, at least about $2$ $cm^3$ or greater, at least about $3$ $cm^3$ or greater, at least about $4$ $cm^3$ or greater, at least about $5$ $cm^3$ or greater, at least about $6$ $cm^3$ or greater, at least about $7$ $cm^3$ or greater, at least about $8$ $cm^3$ or greater, at least about $9$ $cm^3$ or greater, at least about $10$ $cm^3$ or greater, at least about $11$ $cm^3$ or greater, at least about $12$ $cm^3$ or greater, at least about $13$ $cm^3$ or greater, at least about $14$ $cm^3$ or greater, at least about $15$ $cm^3$ or greater, at least about $16$ $cm^3$ or greater, at least about $17$ $cm^3$ or greater, at least about 18 cm³ or greater, at least about 19 cm³ or greater, or at least about 20 cm³ or greater. In certain embodiments, a harvested tumor cell source may be at least about 0.2 cm³ to about 0.3 cm³ or greater, at least about 0.3 cm³ to about 0.4 cm³ or greater, at least about 0.4 cm³ to about 0.5 cm³ or greater, at least about 0.5 cm³ to about 1 cm³ or greater, at least about 1 cm³ to about 2 cm³ or greater, at least about 2 cm³ to about 3 cm³ or greater, at least about 3 cm³ to about 4 cm³ or greater, at least about 4 cm³ to about 5 cm³ or greater, at least about 5 cm³ to about 6 cm³ or greater, at least about 6 cm³ to about 7 cm³ or greater, at least about 7 cm³ to about 8 cm³ or greater, at least about 8 cm³ to about 9 cm³ or greater, at least about 9 cm³ to about 10 cm³ or greater, at least about 10 cm³ to about 11 cm³ or greater, at least about 11 cm³ to about 12 cm³ or greater, at least about 12 cm³ to about 13 cm³ or greater, at least about 13 cm³ to about 14 cm³ or greater, at least about 14 cm³ to about 15 cm³ or greater, at least about 15 cm³ to about 16 cm³ or greater, at least about 16 cm³ to about 17 cm³ or greater, at least about 17 cm³ to about 18 cm³ or greater, 18 cm³ to about 19 cm³ or greater, or at least about 19 cm³ to about 20 cm³ or greater.

It is appreciated that one skilled in the art would be able to select an appropriate method for separating tumor cells from non-tumor cell types for purposes of the present disclosure. It is also appreciated that one skilled in the art would be able to select an appropriate method to culture and expand the isolated tumor cells for purposes of the present disclosure. In one embodiment, a harvested tumor cell source may have enough cells to be isolated and amplified. Preferably, the harvested tumor cell source should have between at least about 0.5 million cells to at least about 60 million cells or greater, at least about 5 million cells to at least about 55 million cells or greater, at least about 10 million cells to at least about 50 million cells or greater, at least about 15 million cells to at least about 50 million cells or greater, at least about 20 million cells to at least about 50 million cells or greater, at least about 25 million cells to at least about 50 million cells or greater, at least about 30 million cells to at least about 40 million cells or greater, or at least about 45 million cells to at least about 45 million cells or greater. In one embodiment, tumor cells may be expanded in culture to obtain at least about 0.5 million cells, at least about 1 million cells, at least about 5 million cells, at least about 10 million cells, at least about 15 million cells, at least about 20 million cells, at least about 25 million cells, at least about 30 million cells, 35 million cells, at least about 40 million cells, at least about 45 million cells, at least about 50 million cells, at least about 55 million cells, at least about 60 million cells, or greater. In another embodiment, tumor cells may be expanded in culture to obtain at least about 0.5 million cells to at least about 1 million cells, at least about 1 million cells to at least about 5 million cells, at least about 5 million cells to at least about 10 million cells, at least about 10 million cells to at least about 15 million cells, at least about 15 million cells to at least about 20 million cells, at least about 20 million cells to at least about 25 million cells, at least about 25 million cells to at least about 30 million cells, at least about 30 million cells to at least about 35 million cells, 35 million cells to at least about 40 million cells, at least about 40 million cells to at least about 45 million cells, at least about 45 million cells to at least about 50 million cells, at least about 50 million cells to at least about 55 million cells, at least about 55 million cells to at least about 60 million cells.

(ii) Incubation with Deglycosylating Agents

A method of the present disclosure comprises incubating tumor cells with one or more deglycosylating agents and/or glycosylation inhibitors, wherein after the incubation a majority of tumor cell membrane is deglycosylated. In preferred forms, a majority or at least 50% of the tumor cell membrane is deglycosylated. In other preferred forms, at least about 55% or more of the tumor cell membrane is deglycosylated. More preferably, at least about 65% or more of the tumor cell membrane is deglycosylated. Still more preferably, at least about 75% or more of the tumor cell membrane is deglycosylated. Still more preferably, at least about 85% or more of the tumor cell membrane is deglycosylated. Ideally, at least about 95% or more of the tumor cell membrane is deglycosylated. In one embodiment, at least about 55% to 95% or greater, at least about 65% to 95% or greater, at least about 75% to 95% or greater, at least about 85% to 95% or greater, or at least about 90% to 95% or greater of tumor cell membrane is deglycosylated. The percentage of tumor cell membrane that is deglycosylated refers to the percentage of CFGs or glycan shield that is disrupted, destroyed, or prevented from forming.

In a preferable embodiment, tumor cells may maintain viability after incubation with one or more deglycosylating agents and/or glycosylation inhibitors. In another embodiment, tumor cells maintain at least about 85% or greater, at least about 90% or greater, at least about 95% or greater, at least about 98% or greater, viability after incubation with one or more deglycosylating agents and/or glycosylation inhibitors. In another embodiment, the membrane of the tumor cell maintains integrity after incubation with one or more deglycosylating agents and/or glycosylation inhibitors. In another embodiment, the membrane of the tumor cell maintains at least about 85% or greater, at least about 90% or greater, at least about 95% or greater, at least about 98% or greater, integrity after incubation with one or more deglycosylating agents and/or glycosylation inhibitors in comparison to a tumor cell that has not been incubated with one or more deglycosylation agents and/or glycosylation inhibitors. In one embodiment, membrane permeability of tumor cells after incubation with one or more deglycosylation agents and/or glycosylation inhibitors is increased compared to membranes of tumors cells not incubated with one or more deglycosylation agents and/or glycosylation inhibitors. In preferred embodiments, membrane permeability may be increased at least about 10% or greater, at least about 15% or greater, at least about 20% or greater, at least about 25% or greater, at least about 30% or greater, at least about 35% or greater, at least about 40% or greater, at least about 45% or greater, at least about 50% or greater, at least about 55% or greater, at least about 60% or greater, at least about 65% or greater, at least about 70% or greater, at least about 75% or greater, at least about 80% or greater, at least about 85% or greater, at least about 90% or greater, at least about 95% or greater, or at least about 98% or greater compared to cell membranes of tumor cells not incubated with one or more deglycosylation agents and/or glycosylation inhibitors. In another embodiment, the cell membrane permeability of tumor cells after incubation with one or more deglycosylation agents and/or glycosylation inhibitors may be increased at least about 10% to 98% or greater, at least 25% to 98% or greater, or at least 50% to 95% or greater compared to cell membranes of tumor cells not incubated with one or more deglycosylation agents and/or glycosylation inhibitors.

In one embodiment, N-linked glycosylation of the tumor cell membrane may be disrupted. In another embodiment, O-linked glycosylation of the tumor cell membrane may be disrupted. In yet another embodiment, C-linked glycosylation of the tumor cell membrane may be disrupted. In still another embodiment, glypiation of the tumor cell membrane may be disrupted. In another embodiment, O-linked glycosylation may be disrupted. In another embodiment multiple glycosidic linkages on the tumor cell membrane may be disrupted comprising of N-, O-, and C-linked glycosylation, glypiation, and phosphoglycosylation.

In one embodiment, deglycosylating agents may be one or more deglycosylating enzymes. As used herein, a "deglycosylating enzyme" refers to an enzyme that modifies or removes glycans from glycoproteins presented on the tumor cell membrane. In one embodiment, one or more deglycosylating enzymes may be a glycoside hydrolase with an EC number of EC 3.2.1. In another embodiment, deglycosylating enzymes may be a neuraminidase with an EC number of EC 3.2.1.18. In another embodiment, deglycosylating enzymes may be a galactosidase with an EC number of EC 3.2.1.23. In still another embodiment, deglycosylating enzymes may be an exoglycosidase with an EC number of EC 3.2.1.25. In another embodiment, deglycosylating enzymes may be an endoglycosidase with an EC number of EC 3.2.1.96. In another embodiment, deglycosylating enzymes may be an O-Glycosidase with an EC number of EC 3.2.1.97. In yet another embodiment, deglycosylating enzymes may be an amidase with an EC number of EC 3.5.1.52. In certain embodiments, a deglycosylating enzyme may be selected from the non-limiting group consisting of a *Clostridium perfringens* neuraminidase, *Vibrio cholerae* neuraminidase, *Arthrobacter ureafaciens* neuraminidase, *Streptococcus pneumonia* neuraminidase, *Enterococcus faecalis* O-Glyco sidase, *Streptococcus pneumonia* β1-4 galactosidase, recombinant endo-β-galactosidase, and recombinant PNGase F. One of skill in the art would understand that the amount of the one or more deglycosylating enzymes used is generally determined by the volume of tumor cells to be deglycosylated. In certain embodiments, tumor cells may be incubated with at least two, at least three, at least four, at least five, or at least six or more distinct deglycosylating enzymes.

In one embodiment, deglycosylating agents may be one or more glycosylation inhibitors. As used herein, a "glycosylation inhibitor" refers to a compound that blocks glycosylation of proteins on the tumor cell membrane. In one embodiment, one or more glycosylation inhibitors may be a natural product. In another embodiment, one or more glycosylation inhibitors may be a synthesized product. In another embodiment, one or more glycosylation inhibitors may interfere with the steps involved in the process of glycosylation. In another embodiment, one or more glycosylation inhibitors may inhibit N-glycosylation synthesis. In another embodiment, one or more glycosylation inhibitors may inhibit O-glycosylation synthesis. In another embodiment, one or more glycosylation inhibitors may inhibit glycosphingolipid synthesis. In another embodiment, one or more glycosylation inhibitors may block glycosyltransferase activity. In another embodiment, one or more glycosylation inhibitors may block glucosylceramide synthetase activity. In another embodiment, one or more glycosylation inhibitors may belong to a class of nucleoside antibiotics. In another embodiment, one or more glycosylation inhibitors may be a plant alkaloid. In certain embodiments, a glycosylation inhibitor may be selected from the non-limiting group consisting of tunicamycin, amphomycin, castano spermine, deoxynojirimycin, australine, swainsonine, deoxymannojirimycin, kifunensin, benzyl 2-acetamido-2-deoxy-a-D-galactopyranoside, D-threo-1-phenyl-2-decanoylamino-3-morpholino-1-propanol, PUGNAc, NAG-thiazoline, GlcNAcstatin, N-butyldeoxynojirimycin, and Neu5Ac-2-ene. One of skill in the art would understand that the concentration of the one or more glycosylation inhibitors used should be determined by the volume of tumor cells to be deglycosylated. In certain embodiments, tumor cells may be incubated with at least two, at least three, at least four, at least five, or at least six or more glycosylation inhibitors.

In some preferred embodiments, one or more deglycosylating enzymes may be combined with one or more glycosylation inhibitors as described above and each are referred to herein as "deglycosylating agents".

To deglycosylate tumor cells, cells may be suspended in cell culture media containing one or more deglycosylating agents and/or glycosylation inhibitors. In one embodiment, the tumor cells may be incubated with one or more deglycosylating agents and/or glycosylation inhibitors for a time sufficient to deglycosylate the tumor cell membrane as described above. In some instances, the incubation period may be for at least about 30 minutes, 1 hour, 2 hours, 3 hours, at least 4 hours, at least 5 hours, or greater, as well as the ranges created by two or more of these options (i.e. 30 minutes to 5 hours, 2 hours to 4 hours, 1 hour to 5 hours, etc.). In another embodiment, the tumor cells may be incubated with one or more deglycosylating agents and/or glycosylation inhibitors at an appropriate temperature sufficient to permit deglycosylation of the tumor cell membrane as described above. In some preferred forms, the incubation temperature may be about 12° C. to 42° C., 15° C. to 42° C., 20° C. to 42° C., 25° C. to 42° C., 32° C. to 42° C., at about 34° C. to 40° C., or at about 36° C. to 38° C. In another embodiment, the incubation period may be stopped by washing the tumor cells in order to remove the deglycosylating agents and/or glycosylation inhibitors from the tumor cells. It is appreciated that one skilled in the art would be able to select an appropriate method for washing tumor cells for purposes of the present disclosure.

Another embodiment of the present disclosure compromises resuspending tumor cells in an aqueous buffer after washing the cells. In one embodiment, the aqueous buffer may be sodium phosphate buffer. In one embodiment, the aqueous buffer may contain a solute. In certain embodiments, the solute may be at least about 0.3 M to 0.1 M, at least about 0.2 M to 0.15 M, or at least about 0.15 M of a chloride, preferably sodium chloride. In another embodiment, the pH of the aqueous buffer may be about 4 to 7, may be about 5.5 to 6.5, or may be at least about 6. In another embodiment, the aqueous buffer may contain a gentle oxidizing agent. In some embodiments, the gentle oxidizing agent may be present in a sufficient amount to deglycosylate the tumor cell membrane. In certain embodiments, the gentle oxidizing agent may be present at least about 5 mM to 100 mM, 10 mM to 40 mM, at least about 40 mM to 75 mM, at least about 45 mM to 60 mM, or at least about 50 mM. In yet another embodiment, the resuspended tumor cells may be incubated in an aqueous buffer containing a gentle oxidizing agent for a time sufficient to deglycosylate the tumor cell membrane. In some preferred embodiments, the incubation time may be at least 0.5 to at least 3 hours, about at least 0.5 to 2 hours, or about at least 1 hour. In certain embodiments, the incubation with a gentle oxidizing agent may occur at a temperature that is sufficient to deglycosylate the tumor cell membrane. In preferred embodiments, the incubation temperature is between about 15° C. to 35° C., 20° C. to 32° C., at least 20° C. to 30° C., at least 22° C. to 25° C., or at least 23° C. In other embodiments, the incubation may occur in the absence of light. In some embodiments, the gentle oxidizing agent may be sodium metaperiodate. In another embodiment, the incubation of resuspended tumor cells in an aqueous buffer containing a gentle oxidizing agent may be terminated. In some embodiments, oxidation may be terminated by addition of a solution known to end the oxidation process. In preferred forms, the termination solution is preferably selected from the group, sodium sulfite, sodium bicarbonate, glycerol, or ethylene glycol. In a preferred embodiment, oxidation may be terminated by addition of ethylene glycol. In another preferred embodiment, the incubation of resuspended tumor cells in an aqueous buffer containing a gentle oxidizing agent may be terminated by the addition of at least about 25 μl to 75 μl, 45 μl to 55 μl, or 50 μl of ethylene glycol per milliliter of aqueous buffer.

(iii) Lysis of Deglycosylated Tumor Cells and Storage Thereof

A method of the present disclosure compromises lysing tumor cells following incubation with one or more deglycosylating agents, wherein after tumor cell lysis, the cellular lysate is stored. It is appreciated that one skilled in the art would be able to select an appropriate method for lysing tumor cells for purposes of the present disclosure. A non-limiting example of a method of tumor cell lysis may be that tumor cells undergo one or more freeze-thaw cycles. In certain embodiments, tumor cells may be frozen at least about −70° C. to −90° C., at least about −75° C. to −85° C., or at least about −80° C. In other certain embodiments, tumor cells may be thawed at least about 20° C. to 50° C., at least about 35° C. to 40° C., or at least about 37° C. In one embodiment, tumor cells may be subjected to about 2 to 7 freeze-thaw cycles, about 3 to 6 freeze-thaw cycles, about 4 to 5 freeze-thaw cycles, or about 5 freeze-thaw cycles.

Methods of storing tumor cells and/or lysed tumor cells are known in the art. Lysed tumor cells may be immediately stored between about 2° C. to 8° C., about 3° C. to 5° C., about 4° C. to 5, or about 4° C. In another embodiment, lysed tumor cells may be stored for up to 6 weeks, up to 5 weeks, at least 4 weeks, at least 3 weeks, at least 2 weeks, or up to least 1 day, at least 2 days, at least 3 days, at least 4 days, at least 5 days, at least 6 days, at least 7 days or greater at a temperature between about 2° C. to 8° C. In yet another embodiment, lysed tumor cells may be stored up to about 1 to 7 days, at least 2 to 6 days, at least 3 to 5 days, at least 3 to 4 days or greater at least about 2° C. to 8° C. In one embodiment of the present disclosure, lysed tumor cells may be immediately stored at least about −50° C. to −90° C., at least about −60° C. to −85° C., at least about −75° C. to −85, or at least about −80° C. In another embodiment, lysed tumor cells may be stored up to least about 1 month, at least about 6 months, at least about 1 year, at least about 2 years, at least about 3 years, at least about 4 years, at least about 5 years or greater at least about −50° C. to −90° C.

(iv) Combining Deglycosylated Tumor Cell Lysate with an Adjuvant System to Form a Vaccine A method of the present disclosure also comprises combining deglycosylated tumor cell lysate with an adjuvant system to form a vaccine. As described herein, an "adjuvant system" is at least one adjuvant, or at least one immunomodulator, or a combination of adjuvants and immunomodulators.

"Adjuvants" as used herein are agents that enhance the immune response of an antigen. In one embodiment, one or more adjuvants may be a particulate adjuvant. In another embodiment, one or more adjuvants may be an emulsion. In some embodiments, one or more adjuvants may be a water-in-oil emulsion, oil-in-water emulsion, water-in-oil-in-water emulsion. The emulsion can be based in particular on light liquid paraffin oil (European Pharmacopea type); isoprenoid oil such as squalane or squalene oil resulting from the oligomerization of alkenes, in particular of isobutene or decene; esters of acids or of alcohols containing a linear alkyl group, more particularly plant oils, ethyl oleate, propylene glycol di-(caprylate/caprate), glyceryl tri-(caprylate/caprate) or propylene glycol dioleate; esters of branched fatty acids or alcohols, in particular isostearic acid esters. The oil is used in combination with emulsifiers to form the emulsion. The emulsifiers are preferably nonionic surfactants, in particular esters of sorbitan, of mannide (e.g. anhydromannitol oleate), of glycol, of polyglycerol, of propylene glycol and of oleic, isostearic, ricinoleic or hydroxystearic acid, which are optionally ethoxylated, and polyoxypropylene-polyoxyethylene copolymer blocks, in particular the Pluronic products, especially L121. See Hunter et al., The Theory and Practical Application of Adjuvants (Ed.Stewart-Tull, D. E. S.). JohnWiley and Sons, NY, pp 51-94 (1995) and Todd et al., Vaccine 15:564-570 (1997). In still another embodiment, one or more adjuvants may be a liposome. In yet another embodiment, one or more adjuvants may be a microsphere of biodegradable polymers. In another embodiment, one or more adjuvants may be an immunomodulator. In one embodiment, an adjuvant system of the present disclosure may be any combination of adjuvants and immunomodulators. Non-limiting examples of immunomodulators comprise monophosphoryl lipid A, bark-saponin Quil A, dsRNA analogues, and N-acetyl muramyl-L-alanyl-D-isoglutamine. Further suitable adjuvant systems useful to the present disclosure include, but are not limited to, the RIBI adjuvant system (Ribi Inc.), Block co-polymer (CytRx, Atlanta Ga.), SAF-M (Chiron, Emeryville Calif.), AS15, MF59, Avridine lipid-amine adjuvant, heat-labile enterotoxin from *E. coli* (recombinant or otherwise), cholera toxin, IMS 1314, GLA-SE, IC31, CAF01, ISCOMs, or muramyl dipeptide among many others. In certain preferred embodiments, the adjuvant system may be AS01. In another preferred embodiment, the adjuvant system may be AS02. In yet another preferred embodiment, the adjuvant system may be AS03. In an ideal embodiment, the adjuvant system may be AS04.

A method of this disclosure comprises combining deglycosylated tumor cell lysates with an adjuvant system to form a vaccine. In on embodiment, lysates from about at least 0.5 to 100 million or greater, at least 5 to 80 million or greater, at least 10 to 70 million or greater, at least 15 to 65 million or greater, at least 20 to 60 million or greater, at least 30 to 50 million or greater, at least 40 to 50 million or greater, or at least 45 to 50 million or greater deglycosylated tumor cells may be mixed with an adjuvant system.

In one embodiment, vaccines may be immediately stored between about 2° C. to 8° C., about 3° C. to 5° C., about 4° C. to 5, or at about 4° C. In another embodiment, vaccines may be stored up to least about 1 day, at least about 1 week, at least about 2 weeks, at least about 1 month, at least about 3 months, at least about 6 months, at least about 1 year or more at a temperature between about 2° C. to 8° C. In yet another embodiment, vaccines may be stored up to least about 1 to about 7 days, at least about 1 to about 2 weeks, at least about 2 weeks to about 1 month, at least about 1 month to about 3 months, at least about 3 months to about 6 months, at least about 6 months to about 1 year or more at a temperature of about 2° C. to 8° C.

(b) Administering an Adjuvanted, Deglycosylated Autologous Tumor Composition as a Vaccine and as a Treatment One embodiment of the present disclosure provides methods of administering an adjuvanted, deglycosylated autologous tumor composition to a patient for treatment of cancer. The method comprises one or more inoculations over an appropriate range of time wherein at least about 5% or greater of tumor growth may be impaired compared to tumor growth in an untreated patient with identical disease condition and predicted outcome.

(i) Delivery of Adjuvanted, Deglycosylated Autologous Tumor Vaccine and Treatment.

It is appreciated that one skilled in the art would be able to select an appropriate device for adjuvanted, deglycosylated autologous tumor vaccine delivery to the patient for purposes of the present disclosure. Non-limiting examples of a device appropriate for vaccine delivery may be conventional injection, injection with hollow microneedles and/or solid microneedles, electroporation systems, needle-free jet injection, ballistic particle-mediated delivery, and electroporation.

In an embodiment of the present disclosure, the delivery route may be selected to produce the appropriate immune response. In one embodiment, the delivery route may be subcutaneous. In another embodiment, the delivery route may be intradermal. In yet another embodiment, the delivery route may be transdermal. In still another embodiment, the delivery route may be intramuscular. In an additional embodiment, the delivery route may be intralymphatic. It is appreciated that one skilled in the art would be able to select an appropriate route for vaccine delivery for purposes of the present disclosure.

In an embodiment of the present disclosure, one dose of adjuvanted, deglycosylated autologous tumor vaccine may be at least about 0.05 ml or greater to at least about 1.0 ml or greater, at least about 0.2 ml or greater to at least about 0.8 ml or greater, at least about 0.4 ml or greater to at least about 0.6 ml or greater. In another embodiment of the present disclosure, one dose of adjuvanted, deglycosylated autologous tumor vaccine may be at least about 0.05 ml or greater, at least about 0.1 ml or greater, at least about 0.2 ml or greater, at least about 0.3 ml or greater, at least about 0.4 ml or greater, at least about 0.5 ml or greater, at least about 0.6 ml or greater, at least about 0.7 ml or greater, at least about 0.8 ml or greater, at least about 0.9 ml or greater, at least about 1.0 ml or greater. In another embodiment of the present disclosure, one dose of adjuvanted, deglycosylated autologous tumor vaccine may be at least about 0.05 ml or greater to at least about 0.1 ml or greater, at least about 0.1 ml or greater to at least about 0.2 ml or greater, at least about 0.2 ml or greater to at least about 0.3 ml or greater, at least about 0.3 ml or greater to at least about 0.4 ml or greater, at least about 0.4 ml or greater to at least about 0.5 ml or greater, at least about 0.5 ml or greater to at least about 0.6 ml or greater, at least about 0.6 ml or greater to at least about 0.7 ml or greater, at least about 0.7 ml or greater to at least about 0.8 ml or greater, at least about 0.8 ml or greater to at least about 0.9 ml or greater, at least about 0.9 ml or greater to at least about 1.0 ml or greater.

In another embodiment of the present disclosure, one dose of adjuvanted, deglycosylated autologous tumor vaccine may contain lysate in amounts as described above, or from at least about 5 to 60 million or more, about at least about 20 to 50 million or more, about at least about 40 to 50 million or more, or about at least about 45 to 50 million or more deglycosylated tumor cells. In another embodiment, one dose of tumor vaccine may contain lysate from an amount of deglycosylated tumor cells as described above, or at least about 5 million or more, at least about 10 million or more, at least about 15 million or more, at least about 20 million or more, at least about 25 million or more, at least about 30 million or more, at least about 35 million or more, at least about 40 million or more, at least about 45 million or more, at least about 50 million or more, at least about 55 million or more, at least about 60 million or more deglycosylated tumor cells. In another embodiment, one dose of tumor vaccine may contain lysate from an amount of tumor cells as described above, or at least about 5 million or more to least about 10 million or more, at least about 10 million or more to least about 10 million or more, at least about 15 million or more to least about 20 million or more, at least about 20 million or more to least about 25 million or more, at least about 25 million or more to at least about 30 million or more, at least about 30 million or more to at least about 35 million or more, at least about 35 million or more to at least about 40 million or more, at least about 40 million or more to at least about 45 million or more, at least about 45 million or more to at least about 50 million or more, at least about 50 million or more to at least about 55 million or more, at least about 55 million or more to at least about 60 million or more deglycosylated tumor cells.

In another embodiment, a patient may be inoculated with a dose of the adjuvanted, deglycosylated autologous tumor vaccine once or multiple times. In another embodiment, inoculation of the patient with a dose of the tumor vaccine may occur multiple times until desired results are observed. It is appreciated that one skilled in the art would be able to select an appropriate number of inoculations to achieve the desired response for purposes of the present disclosure. In preferred embodiments, inoculation of the patient with a dose of the adjuvanted, deglycosylated autologous tumor vaccine may occur once, up to two times, up to three times, up to four times, or up to five times. One preferred dose regimen comprises four inoculations.

In one embodiment of the present disclosure, a patient may be inoculated with a dose of the adjuvanted, deglycosylated autologous tumor vaccine multiple times at irregular intervals. In another embodiment, a patient may be inoculated with a dose of the tumor vaccine multiple times at regular intervals. In another embodiment, a patient may be inoculated with a dose of the tumor vaccine multiple times at about at least 1-week or greater, at least 2-week or greater, at least 3-week or greater, at least 4-week or greater, at least 5-week or greater, at least 6-week or greater intervals. In another embodiment, a patient may be inoculated with a dose of the tumor vaccine multiple times at about at least 1-week or greater, at least 2-week or greater to at least 3-week or greater, at least 3-week or greater to at least 4-week or greater, at least 4-week or greater to at least 5-week or greater, at least 5-week or greater to at least 6-week or greater intervals. It is appreciated that one skilled in the art would be able to select an appropriate interval of inoculation regimen to achieve the desired response for purposes of the present disclosure.

In another embodiment of the present disclosure, one or more doses of the adjuvanted, deglycosylated autologous tumor vaccine may be administered as a booster vaccine following initial treatment regimen. In one embodiment, one or more doses of the tumor vaccine may be administered for the lifetime of the patient. In one embodiment, a dose of the tumor vaccine may be administered as a booster vaccine at least every 3 months or more, at least every 6 months or more, at least every year or more, at least every 2 years or more, at least every 3 years or more following initial treatment regimen. It is appreciated that one skilled in the art would be able to select an appropriate interval of booster inoculation regimen to achieve the desired response for purposes of the present disclosure.

(ii) Combination Therapies Involving Adjuvanted, Deglycosylated Autologous Tumor Vaccine and Treatment.

Another embodiment of the present disclosure may be to combine the adjuvanted, deglycosylated autologous tumor vaccine and treatment prepared as described above with one or more additional therapies that are appropriate for cancer treatment. In one embodiment, the adjuvanted, deglycosylated autologous tumor vaccine, containing complete tumor cell lysate, may be combined with another vaccine containing one or more tumor antigens. In another embodiment, the adjuvanted, deglycosylated autologous tumor vaccine, containing complete tumor cell lysate, may be combined with another vaccine containing one or more tumor growth factor receptors. In other embodiments, implementation of an adjuvanted, deglycosylated autologous tumor vaccine and treatment may be combined with standard-of-care cancer therapies. As used herein, "standard-of-care cancer therapies" entail tone or more treatments accepted by medical experts as a proper treatment for a certain type of disease and that is widely used by healthcare professionals. These standard of care cancer therapies include chemotherapy as well as radiation therapy. It is appreciated that one skilled in the art would be able to select one or more appropriate standard-of-care cancer therapies to use in combination with the tumor vaccine described in the present disclosure for the desired outcome.

(iii) Disease Outcomes Following Inoculation with an Adjuvanted, Deglycosylated Autologous Tumor Vaccine and Treatment.

The method of the present disclosure comprises one or more inoculations over an appropriate range of time wherein tumor growth may be impaired compared to tumor growth in an untreated patient with identical disease condition and predicted outcome. In one embodiment, tumor growth may be stopped following treatment with the tumor vaccine described herein. In other embodiments, tumor growth may be impaired at least about 5% or greater to at least about 100%, at least about 10% or greater to at least about 95% or greater, at least about 20% or greater to at least about 80% or greater, at least about 40% or greater to at least about 60% or greater compared to an untreated patient with identical disease condition and predicted outcome. In other words, tumors in patients treated using the methods and compositions of the disclosure have tumors that grow at least 5% less (or more as described above) when compared to an untreated patient with identical disease condition and predicted outcome. In some embodiments, tumor growth may be impaired at least about 5% or greater, at least about 10% or greater, at least about 15% or greater, at least about 20% or greater, at least about 25% or greater, at least about 30% or greater, at least about 35% or greater, at least about 40% or greater, at least about 45% or greater, at least about 50% or greater, at least about 55% or greater, at least about 60% or greater, at least about 65% or greater, at least about 70% or greater, at least about 75% or greater, at least about 80% or greater, at least about 85% or greater, at least about 90% or greater, at least about 95% or greater, at least about 100% compared to an untreated patient with identical disease condition and predicted outcome. In additional embodiments, tumor growth may be impaired at least about 5% or greater to at least about 10% or greater, at least about 10% or greater to at least about 15% or greater, at least about 15% or greater to at least about 20% or greater, at least about 20% or greater to at least about 25% or greater, at least about 25% or greater to at least about 30% or greater, at least about 30% or greater to at least about 35% or greater, at least about 35% or greater to at least about 40% or greater, at least about 40% or greater to at least about 45% or greater, at least about 45% or greater to at least about 50% or greater, at least about 50% or greater to at least about 55% or greater, at least about 55% or greater to at least about 60% or greater, at least about 60% or greater to at least about 65% or greater, at least about 65% or greater to at least about 70% or greater, at least about 70% or greater to at least about 75% or greater, at least about 75% or greater to at least about 80% or greater, at least about 80% or greater to at least about 85% or greater, at least about 85% or greater to at least about 90% or greater, at least about 90% or greater to at least about 95% or greater, at least about 95% or greater to at least about 100% compared to an untreated patient with identical disease condition and predicted outcome. In some forms, treatment of tumors results in a shrinking of a tumor in comparison to the starting size of the tumor. This shrinking is at least about 5% or greater to at least about 10% or greater, at least about 10% or greater to at least about 15% or greater, at least about 15% or greater to at least about 20% or greater, at least about 20% or greater to at least about 25% or greater, at least about 25% or greater to at least about 30% or greater, at least about 30% or greater to at least about 35% or greater, at least about 35% or greater to at least about 40% or greater, at least about 40% or greater to at least about 45% or greater, at least about 45% or greater to at least about 50% or greater, at least about 50% or greater to at least about 55% or greater, at least about 55% or greater to at least about 60% or greater, at least about 60% or greater to at least about 65% or greater, at least about 65% or greater to at least about 70% or greater, at least about 70% or greater to at least about 75% or greater, at least about 75% or greater to at least about 80% or greater, at least about 80% or greater to at least about 85% or greater, at least about 85% or greater to at least about 90% or greater, at least about 90% or greater to at least about 95% or greater, at least about 95% or greater to at least about 100% (meaning that the tumor is completely gone after treatment) compared to the starting size of the tumor.

The method of the present disclosure comprises one or more inoculations over an appropriate range of time wherein the presence of tumor markers is lower compared to the presence of tumor markers in an untreated patient with identical disease condition and predicted outcome. As used herein "tumor markers" are defined as substances produced by cancer or by other cells of the body in response to cancerous conditions. Non-limiting examples of tumor markers include alpha-fetoprotein, beta-2-microglobulin, beta-human chorionic gonadotropin, BCR-ABL fusion gene, CA19-9, CD20, HE4, lactate dehydrogenase, prostate-specific antigen, and various others. In one embodiment of the present disclosure, the presence of tumor markers may be ablated following treatment with the tumor vaccine described herein. In other embodiments, the presence of tumor markers may be decreased at least about 5% or greater to at least about 100%, at least about 10% or greater to at least about 95% or greater, at least about 20% or greater to at least about 80% or greater, at least about 40% or greater to at least about 60% or greater compared to an untreated patient with identical disease condition and predicted outcome. In some embodiments, the presence of tumor markers may be decreased at least about 5% or greater, at least about 10% or greater, at least about 15% or greater, at least about 20% or greater, at least about 25% or greater, at least about 30% or greater, at least about 35% or greater, at least about 40% or greater, at least about 45% or greater, at least about 50% or greater, at least about 55% or greater, at least about 60% or greater, at least about 65% or greater, at least about 70% or greater, at least about 75% or greater, at least about 80% or greater, at least about 85% or greater, at least about 90% or greater, at least about 95% or greater, at least about 100% compared to an untreated patient with identical disease condition and predicted outcome. In additional embodiments, the presence of tumor markers may be decreased at least about 5% or greater to at least about 10% or greater, at least about 10% or greater to at least about 15% or greater, at least about 15% or greater to at least about 20% or greater, at least about 20% or greater to at least about 25% or greater, at least about 25% or greater to at least about 30% or greater, at least about 30% or greater to at least about 35% or greater, at least about 35% or greater to at least about 40% or greater, at least about 40% or greater to at least about 45% or greater, at least about 45% or greater to at least about 50% or greater, at least about 50% or greater to at least about 55% or greater, at least about 55% or greater to at least about 60% or greater, at least about 60% or greater to at least about 65% or greater, at least about 65% or greater to at least about 70% or greater, at least about 70% or greater to at least about 75% or greater, at least about 75% or greater to at least about 80% or greater, at least about 80% or greater to at least about 85% or greater, at least about 85% or greater to at least about 90% or greater, at least about 90% or greater to at least about 95% or greater, at least about 95% or greater to at least about 100% compared to an untreated patient with identical disease condition and predicted outcome.

The method of the present disclosure comprises one or more inoculations over an appropriate range of time wherein the cancer life expectancy may be improved compared to the cancer life expectancy of an untreated patient with identical disease condition and predicted outcome. As used herein, "cancer life expectancy" is defined as the time at which 50 percent of patients are alive and 50 percent have passed away. In one embodiment of the present disclosure, cancer life expectancy may be indefinite following treatment with the tumor vaccine described herein. In other embodiments, cancer life expectancy may be increased at least about 5% or greater to at least about 100%, at least about 10% or greater to at least about 95% or greater, at least about 20% or greater to at least about 80% or greater, at least about 40% or greater to at least about 60% or greater compared to an untreated patient with identical disease condition and predicted outcome. In some embodiments, cancer life expectancy may be increased at least about 5% or greater, at least about 10% or greater, at least about 15% or greater, at least about 20% or greater, at least about 25% or greater, at least about 30% or greater, at least about 35% or greater, at least about 40% or greater, at least about 45% or greater, at least about 50% or greater, at least about 55% or greater, at least about 60% or greater, at least about 65% or greater, at least about 70% or greater, at least about 75% or greater, at least about 80% or greater, at least about 85% or greater, at least about 90% or greater, at least about 95% or greater, at least about 100% compared to an untreated patient with identical disease condition and predicted outcome. In additional embodiments, cancer life expectancy may be increased at least about 5% or greater to at least about 10% or greater, at least about 10% or greater to at least about 15% or greater, at least about 15% or greater to at least about 20% or greater, at least about 20% or greater to at least about 25% or greater, at least about 25% or greater to at least about 30% or greater, at least about 30% or greater to at least about 35% or greater, at least about 35% or greater to at least about 40% or greater, at least about 40% or greater to at least about 45% or greater, at least about 45% or greater to at least about 50% or greater, at least about 50% or greater to at least about 55% or greater, at least about 55% or greater to at least about 60% or greater, at least about 60% or greater to at least about 65% or greater, at least about 65% or greater to at least about 70% or greater, at least about 70% or greater to at least about 75% or greater, at least about 75% or greater to at least about 80% or greater, at least about 80% or greater to at least about 85% or greater, at least about 85% or greater to at least about 90% or greater, at least about 90% or greater to at least about 95% or greater, at least about 95% or greater to at least about 100% compared to an untreated patient with identical disease condition and predicted outcome.

II. An Adjuvanted, Deglycosylated Autologous Tumor Vaccine and Treatment

One aspect of the present disclosure provides an adjuvanted, deglycosylated autologous tumor vaccine and treatment. The vaccine may be derived from a cancerous lesion harvested from a patient. In an embodiment of the present disclosure, the cancer may be a primary cancer, a metastases, or primary cancer and metastases. In one embodiment, the cancer may be a solid cancer. In another embodiment, the cancer may be a liquid cancer. In some embodiments, the tumor grade of the harvested tissue may be between 1 and 4, may be 1, may be 2, may be 3, or may be 4. Generally speaking, methods of harvesting tumors from patients are known in the art and it is appreciated that one skilled in the art would be able to select one or more appropriate methods to harvest cancerous tissue or cells as described in the present disclosure.

In one embodiment, a harvested tumor cell source to generate the tumor vaccine is large enough to obtain a sample from which the composition can be made. In some embodiments, the tumor cell source may be between about 0.2 cm$^3$ to at least about 20 cm$^3$ or greater, at least 2 cm$^3$ to at least about 18 cm$^3$ or greater, at least 3 cm$^3$ to at least about 15 cm$^3$ or greater, at least 4 cm$^3$ to at least about 12 cm$^3$ or greater, at least 5 cm$^3$ to at least about 10 cm$^3$ or greater, or at least 6 cm$^3$ to at least about 8 cm$^3$ or greater. A harvested tumor cell source may be at least about 1 cm$^3$ or greater, at least about 2 cm$^3$ or greater, at least about 3 cm$^3$ or greater, at least about 4 cm$^3$ or greater, at least about 5 cm$^3$ or greater, at least about 6 cm$^3$ or greater, at least about 7 cm$^3$ or greater, at least about 8 cm$^3$ or greater, at least about 9 cm$^3$ or greater, at least about 10 cm$^3$ or greater, at least about 11 cm$^3$ or greater, at least about 12 cm$^3$ or greater, at least about 13 cm$^3$ or greater, at least about 14 cm$^3$ or greater, at least about 15 cm$^3$ or greater, at least about 16 cm$^3$ or greater, at least about 17 cm$^3$ or greater, at least about 18 cm$^3$ or greater, at least about 19 cm$^3$ or greater, or at least about 20 cm$^3$ or greater. In certain embodiments, a harvested tumor cell source may be at least about 0.2 cm$^3$ to about 0.3 cm$^3$ or greater, at least about 0.3 cm$^3$ to about 0.4 cm$^3$ or greater, at least about 0.4 cm$^3$ to about 0.5 cm$^3$ or greater, at least about 0.5 cm$^3$ to about 1 cm$^3$ or greater, at least about 1 cm$^3$ to about 2 cm$^3$ or greater, at least about 2 cm$^3$ to about 3 cm$^3$ or greater, at least about 3 cm$^3$ to about 4 cm$^3$ or greater, at least about 4 cm$^3$ to about 5 cm$^3$ or greater, at least about 5 cm$^3$ to about 6 cm$^3$ or greater, at least about 6 cm$^3$ to about 7 cm$^3$ or greater, at least about 7 cm$^3$ to about 8 cm$^3$ or greater, at least about 8 cm$^3$ to about 9 cm$^3$ or greater, at least about 9 cm$^3$ to about 10 cm$^3$ or greater, at least about 10 cm$^3$ to about 11 cm$^3$ or greater, at least about 11 cm$^3$ to about 12 cm$^3$ or greater, at least about 12 cm$^3$ to about 13 cm$^3$ or greater, at least about 13 cm$^3$ to about 14 cm$^3$ or greater, at least about 14 cm$^3$ to about 15 cm$^3$ or greater, at least about 15 cm³ to about 16 cm³ or greater, at least about 16 cm³ to about 17 cm³ or greater, at least about 17 cm³ to about 18 cm³ or greater, 18 cm³ to about 19 cm³ or greater, or at least about 19 cm³ to about 20 cm³ or greater.

In one embodiment, a harvested tumor cell source may yield a number of cells as described above or between at least about 0.5 million cells to at least about 100 million cells or greater, at least about 3 million cells to at least about 60 million cells or greater, at least about 5 million cells to at least about 60 million cells or greater, at least about 10 million cells to at least about 60 million cells or greater, at least about 15 million cells to at least about 60 million cells or greater, at least about 20 million cells to at least about 60 million cells or greater, at least about 25 million cells to at least about 50 million cells or greater, at least about 30 million cells to at least about 40 million cells or greater, or at least about 45 million cells to at least about 45 million cells or greater. In one embodiment, tumor cells may be expanded in culture to obtain at least about 0.5 million cells, at least about 1 million cells, at least about 5 million cells, at least about 7 million cells, at least about 10 million cells, at least about 15 million cells, at least about 20 million cells, at least about 25 million cells, at least about 30 million cells, 35 million cells, at least about 40 million cells, at least about 45 million cells, at least about 50 million cells, at least about 55 million cells, at least about 60 million cells, or greater. In another embodiment, tumor cells may be expanded in culture to obtain at least about 0.5 million cells to at least about 60 million cells, at least about 5 million cells to at least about 60 million cells, at least about 7 million cells to at least about 60 million cells, at least about 10 million cells to at least about 15 million cells, at least about 15 million cells to at least about 20 million cells, at least about 20 million cells to at least about 25 million cells, at least about 25 million cells to at least about 30 million cells, at least about 30 million cells to at least about 35 million cells, 35 million cells to at least about 40 million cells, at least about 40 million cells to at least about 45 million cells, at least about 45 million cells to at least about 50 million cells, at least about 50 million cells to at least about 55 million cells, at least about 55 million cells to at least about 60 million cells.

An adjuvanted, deglycosylated autologous tumor vaccine and treatment may be composed of tumor cells wherein a majority of tumor cell membrane may be deglycosylated. In preferred forms, at least about 55% or more of the tumor cell membrane may be deglycosylated. More preferably, at least about 65% or more of the tumor cell membrane may be deglycosylated. Still more preferably, at least about 75% or more of the tumor cell membrane may be deglycosylated. Still more preferably, at least about 85% or more of the tumor cell membrane may be deglycosylated. Ideally, at least about 95% or more of the tumor cell membrane may be deglycosylated. In one embodiment, at least about 55% to 95% or greater, at least about 65% to 95% or greater, at least about 75% to 95% or greater, at least about 85% to 95% or greater, or at least about 90% to 95% or greater of tumor cell membrane may be deglycosylated.

An adjuvanted, deglycosylated autologous tumor vaccine and treatment may be composed of deglycosylated tumor cell lysate that may be stored for vaccine production. It is appreciated that one skilled in the art would be able to select an appropriate method for lysing tumor cells and for storing tumor cells for purposes of the present disclosure. Lysed tumor cells may be immediately stored as described above or at least about 2° C. to 8° C., at least about 3° C. to 5° C., at least about 4° C. to 5, or at least about 4° C. In another embodiment, vaccines may be stored up to least about 1 day, at least about 1 week, at least about 2 weeks, at least about 1 month, at least about 3 months, at least about 6 months, at least about 1 year or more at a temperature between about 2° C. to 8° C. In yet another embodiment, vaccines may be stored up to least about 1 to about 7 days, at least about 1 to about 2 weeks, at least about 2 weeks to about 1 month, at least about 1 month to about 3 months, at least about 3 months to about 6 months, at least about 6 months to about 1 year or more at a temperature of about 2° C. to 8° C. In one embodiment of the present disclosure, lysed tumor cells may be immediately stored at least about −50° C. to −90° C., at least about −60° C. to −85° C., at least about −75° C. to −85, or at least about −80° C. In another embodiment, lysed tumor cells may be stored up to least about 1 month, at least about 6 months, at least about 1 year, at least about 2 years, at least about 3 years, at least about 4 years, at least about 5 years or greater at least about −50° C. to −90° C. An adjuvanted, deglycosylated autologous tumor vaccine and treatment may be composed of deglycosylated tumor cell lysate combined with an adjuvant system. Suitable adjuvant systems useful to the present disclosure are known in the art and are described above. In preferred embodiments, the adjuvant system may be AS01, AS02, and/or AS03. In an ideal embodiment, the adjuvant system may be AS04.

In one embodiment, an adjuvanted, deglycosylated autologous tumor vaccine may be immediately stored as described above or at least about 2° C. to 8° C., at least about 3° C. to 5° C., at least about 4° C. to 5, or at least about 4° C. In another embodiment, vaccines may be stored up to least about 1 day, at least about 1 week, at least about 2 weeks, at least about 1 month, at least about 3 months, at least about 6 months, at least about 1 year or more at a temperature between about 2° C. to 8° C. In yet another embodiment, vaccines may be stored up to least about 1 to about 7 days, at least about 1 to about 2 weeks, at least about 2 weeks to about 1 month, at least about 1 month to about 3 months, at least about 3 months to about 6 months, at least about 6 months to about 1 year or more at a temperature of about 2° C. to 8° C.

It is appreciated that one skilled in the art would be able to select an appropriate device for adjuvanted, deglycosylated autologous tumor vaccine delivery to the patient for purposes of the present disclosure. In an embodiment of the present disclosure, the delivery route may be selected to produce the appropriate immune response. In one embodiment, the delivery route may be subcutaneous. In another embodiment, the delivery route may be intradermal. In yet another embodiment, the delivery route may be transdermal. In still another embodiment, the delivery route may be intramuscular. In an additional embodiment, the delivery route may be intralymphatic. It is appreciated that one skilled in the art would be able to select an appropriate route for vaccine delivery for purposes of the present disclosure.

One dose of an adjuvanted, deglycosylated autologous tumor vaccine and treatment may be composed of a volume as described above or of at least about 0.05 ml or greater to at least about 1.0 ml or greater, at least about 0.2 ml or greater to at least about 0.8 ml or greater, at least about 0.4 ml or greater to at least about 0.6 ml or greater. In another embodiment of the present disclosure, one dose of adjuvanted, deglycosylated autologous tumor vaccine may be at least about 0.05 ml or greater, at least about 0.1 ml or greater, at least about 0.2 ml or greater, at least about 0.3 ml or greater, at least about 0.4 ml or greater, at least about 0.5 ml or greater, at least about 0.6 ml or greater, at least about 0.7 ml or greater, at least about 0.8 ml or greater, at least about 0.9 ml or greater, at least about 1.0 ml or greater. In another embodiment of the present disclosure, one dose of adjuvanted, deglycosylated autologous tumor vaccine may be at least about 0.05 ml or greater to at least about 0.1 ml or greater, at least about 0.1 ml or greater to at least about 0.2 ml or greater, at least about 0.2 ml or greater to at least about 0.3 ml or greater, at least about 0.3 ml or greater to at least about 0.4 ml or greater, at least about 0.4 ml or greater to at least about 0.5 ml or greater, at least about 0.5 ml or greater to at least about 0.6 ml or greater, at least about 0.6 ml or greater to at least about 0.7 ml or greater, at least about 0.7 ml or greater to at least about 0.8 ml or greater, at least about 0.8 ml or greater to at least about 0.9 ml or greater, at least about 0.9 ml or greater to at least about 1.0 ml or greater.

One dose of an adjuvanted, deglycosylated autologous tumor vaccine and treatment may be composed of lysate as described above, or from at least about 0.5 to 60 million or more, about at least about 20 to 50 million or more, about at least about 40 to 50 million or more, or about at least about 45 to 50 million or more deglycosylated tumor cells. In another embodiment, one dose of tumor vaccine may contain lysate from at least about 0.5 million or more, at least about 1 million or more, at least about 5 million or more, at least about 10 million or more, at least about 15 million or more, at least about 20 million or more, at least about 25 million or more, at least about 30 million or more, at least about 35 million or more, at least about 40 million or more, at least about 45 million or more, at least about 50 million or more, at least about 55 million or more, at least about 60 million or more deglycosylated tumor cells. In another embodiment, one dose of tumor vaccine may contain lysate from at least about 0.5 million or more to least about 1 million or more, at least about 1 million or more to least about 5 million or more, at least about 5 million or more to least about 10 million or more, at least about 10 million or more to least about 15 million or more, at least about 15 million or more to least about 20 million or more, at least about 20 million or more to least about 25 million or more, at least about 25 million or more to at least about 30 million or more, at least about 30 million or more to at least about 35 million or more, at least about 35 million or more to at least about 40 million or more, at least about 40 million or more to at least about 45 million or more, at least about 45 million or more to at least about 50 million or more, at least about 50 million or more to at least about 55 million or more, at least about 55 million or more to at least about 60 million or more deglycosylated tumor cells.

In another embodiment of the present disclosure, a treatment regimen composed of an adjuvanted, deglycosylated autologous tumor vaccine and treatment may include inoculation of the patient once or multiple times. In another embodiment, inoculation of the patient with a dose of the tumor vaccine may occur multiple times until desired results are observed. It is appreciated that one skilled in the art would be able to select an appropriate number of inoculations to achieve the desired response for purposes of the present disclosure. In preferred embodiments, inoculation of the patient with a dose of the adjuvanted, deglycosylated autologous tumor vaccine may occur once, up to two times, up to three times, up to four times, up to five times. In another embodiment of the present disclosure, a patient may be inoculated with a dose of the adjuvanted, deglycosylated autologous tumor vaccine multiple times at irregular intervals. In yet another embodiment, a patient may be inoculated with a dose of the tumor vaccine multiple times at regular intervals. In still another embodiment, a patient may be inoculated with a dose of the tumor vaccine multiple times at about at least 2-week or greater, at least 3-week or greater, at least 4-week or greater, at least 5-week or greater, at least 6-week or greater intervals. In another embodiment, a patient may be inoculated with a dose of the tumor vaccine multiple times at about at least 2-week or greater to at least 3-week or greater, at least 3-week or greater to at least 4-week or greater, at least 4-week or greater to at least 5-week or greater, at least 5-week or greater to at least 6-week or greater intervals. It is appreciated that one skilled in the art would be able to select an appropriate interval of inoculation regimen to achieve the desired response for purposes of the present disclosure.

In another embodiment of the present disclosure, a booster vaccine composed of an adjuvanted, deglycosylated autologous tumor vaccine may be administered following initial treatment regimen. In one embodiment, one or more doses of the tumor vaccine may be administered for the lifetime of the patient. In one embodiment, a dose of the tumor vaccine may be administered as a booster vaccine at least every 3 months or more, at least every 6 months or more, at least every year or more, at least every 2 years or more, at least every 3 years or more following initial treatment regimen. It is appreciated that one skilled in the art would be able to select an appropriate interval of booster inoculation regimen to achieve the desired response for purposes of the present disclosure.

In the present disclosure, an adjuvanted, deglycosylated autologous tumor vaccine and treatment may impair growth of cancerous tumors in an inoculated patient compared to an untreated patient with identical disease condition and predicted outcome. In one embodiment, tumor growth may be stopped following treatment with the tumor vaccine described herein. In other embodiments, tumor growth may be impaired at least about 5% or greater to at least about 100%, at least about 10% or greater to at least about 95% or greater, at least about 20% or greater to at least about 80% or greater, at least about 40% or greater to at least about 60% or greater compared to an untreated patient with identical disease condition and predicted outcome. "Impaired tumor growth" refers to a decrease in growth of a tumor in comparison to tumor growth in an untreated patient with identical disease condition and predicted outcome. In some embodiments, tumor growth may be impaired, at least about 5% or greater, at least about 10% or greater, at least about 15% or greater, at least about 20% or greater, at least about 25% or greater, at least about 30% or greater, at least about 35% or greater, at least about 40% or greater, at least about 45% or greater, at least about 50% or greater, at least about 55% or greater, at least about 60% or greater, at least about 65% or greater, at least about 70% or greater, at least about 75% or greater, at least about 80% or greater, at least about 85% or greater, at least about 90% or greater, at least about 95% or greater, at least about 100% compared to an untreated patient with identical disease condition and predicted outcome. In additional embodiments, tumor growth may be impaired at least about 5% or greater to at least about 10% or greater, at least about 10% or greater to at least about 15% or greater, at least about 15% or greater to at least about 20% or greater, at least about 20% or greater to at least about 25% or greater, at least about 25% or greater to at least about 30% or greater, at least about 30% or greater to at least about 35% or greater, at least about 35% or greater to at least about 40% or greater, at least about 40% or greater to at least about 45% or greater, at least about 45% or greater to at least about 50% or greater, at least about 50% or greater to at least about 55% or greater, at least about 55% or greater to at least about 60% or greater, at least about 60% or greater to at least about 65% or greater, at least about 65% or greater to at least about 70% or greater, at least about 70% or greater to at least about 75% or greater, at least about 75% or greater to at least about 80% or greater, at least about 80% or greater to at least about 85% or greater, at least about 85% or greater to at least about 90% or greater, at least about 90% or greater to at least about 95% or greater, at least about 95% or greater to at least about 100% compared to an untreated patient with identical disease condition and predicted outcome. In some forms, treatment of tumors results in a shrinking of a tumor in comparison to the starting size of the tumor. This shrinking is at least about 5% or greater to at least about 10% or greater, at least about 10% or greater to at least about 15% or greater, at least about 15% or greater to at least about 20% or greater, at least about 20% or greater to at least about 25% or greater, at least about 25% or greater to at least about 30% or greater, at least about 30% or greater to at least about 35% or greater, at least about 35% or greater to at least about 40% or greater, at least about 40% or greater to at least about 45% or greater, at least about 45% or greater to at least about 50% or greater, at least about 50% or greater to at least about 55% or greater, at least about 55% or greater to at least about 60% or greater, at least about 60% or greater to at least about 65% or greater, at least about 65% or greater to at least about 70% or greater, at least about 70% or greater to at least about 75% or greater, at least about 75% or greater to at least about 80% or greater, at least about 80% or greater to at least about 85% or greater, at least about 85% or greater to at least about 90% or greater, at least about 90% or greater to at least about 95% or greater, at least about 95% or greater to at least about 100% (meaning that the tumor is completely gone after treatment) compared to the starting size of the tumor.

Also in the present disclosure, an adjuvanted, deglycosylated autologous tumor vaccine and treatment may reduce the presence of one or more tumor markers in an inoculated patient compared to an untreated patient with identical disease condition and predicted outcome. In one embodiment of the present disclosure, the presence of tumor markers may be ablated following treatment with the tumor vaccine described herein. In other embodiments, the presence of tumor markers may be decreased as described above or at least about 5% or greater to at least about 100%, at least about 10% or greater to at least about 95% or greater, at least about 20% or greater to at least about 80% or greater, at least about 40% or greater to at least about 60% or greater compared to an untreated patient with identical disease condition and predicted outcome. In some embodiments, the presence of tumor markers may be decreased at least about 5% or greater, at least about 10% or greater, at least about 15% or greater, at least about 20% or greater, at least about 25% or greater, at least about 30% or greater, at least about 35% or greater, at least about 40% or greater, at least about 45% or greater, at least about 50% or greater, at least about 55% or greater, at least about 60% or greater, at least about 65% or greater, at least about 70% or greater, at least about 75% or greater, at least about 80% or greater, at least about 85% or greater, at least about 90% or greater, at least about 95% or greater, at least about 100% compared to an untreated patient with identical disease condition and predicted outcome. In additional embodiments, the presence of tumor markers may be decreased at least about 5% or greater to at least about 10% or greater, at least about 10% or greater to at least about 15% or greater, at least about 15% or greater to at least about 20% or greater to at least about 20% or greater, at least about 20% or greater to at least about 25% or greater, at least about 25% or greater to at least about 30% or greater, at least about 30% or greater to at least about 35% or greater, at least about 35% or greater to at least about 40% or greater, at least about 40% or greater to at least about 45% or greater, at least about 45% or greater to at least about 50% or greater, at least about 50% or greater to at least about 55% or greater, at least about 55% or greater to at least about 60% or greater, at least about 60% or greater to at least about 65% or greater, at least about 65% or greater to at least about 70% or greater, at least about 70% or greater to at least about 75% or greater, at least about 75% or greater to at least about 80% or greater, at least about 80% or greater to at least about 85% or greater, at least about 85% or greater to at least about 90% or greater, at least about 90% or greater to at least about 95% or greater, at least about 95% or greater to at least about 100% compared to an untreated patient with identical disease condition and predicted outcome.

Within the present disclosure, an adjuvanted, deglycosylated autologous tumor vaccine and treatment may improve the cancer life expectancy of an inoculated patient compared to that of an untreated patient with identical disease condition and predicted outcome. In one embodiment of the present disclosure, cancer life expectancy may be indefinite following treatment with the tumor vaccine described herein. In other embodiments, cancer life expectancy may be increased as described above or at least about 5% or greater to at least about 100%, at least about 10% or greater to at least about 95% or greater, at least about 20% or greater to at least about 80% or greater, at least about 40% or greater to at least about 60% or greater compared to an untreated patient with identical disease condition and predicted outcome. In some embodiments, cancer life expectancy may be increased at least about 5% or greater, at least about 10% or greater, at least about 15% or greater, at least about 20% or greater, at least about 25% or greater, at least about 30% or greater, at least about 35% or greater, at least about 40% or greater, at least about 45% or greater, at least about 50% or greater, at least about 55% or greater, at least about 60% or greater, at least about 65% or greater, at least about 70% or greater, at least about 75% or greater, at least about 80% or greater, at least about 85% or greater, at least about 90% or greater, at least about 95% or greater, at least about 100% compared to an untreated patient with identical disease condition and predicted outcome. In additional embodiments, cancer life expectancy may be increased at least about 5% or greater to at least about 10% or greater, at least about 10% or greater to at least about 15% or greater, at least about 15% or greater to at least about 20% or greater, at least about 20% or greater to at least about 25% or greater, at least about 25% or greater to at least about 30% or greater, at least about 30% or greater to at least about 35% or greater, at least about 35% or greater to at least about 40% or greater, at least about 40% or greater to at least about 45% or greater, at least about 45% or greater to at least about 50% or greater, at least about 50% or greater to at least about 55% or greater, at least about 55% or greater to at least about 60% or greater, at least about 60% or greater to at least about 65% or greater, at least about 65% or greater to at least about 70% or greater, at least about 70% or greater to at least about 75% or greater, at least about 75% or greater to at least about 80% or greater, at least about 80% or greater to at least about 85% or greater, at least about 85% or greater to at least about 90% or greater, at least about 90% or greater to at least about 95% or greater, at least about 95% or greater to at least about 100% compared to an untreated patient with identical disease condition and predicted outcome.

III. A Deglycosylated Autologous Tumor Vaccine Composition and Treatment

In other preferred forms, the composition of the present disclosure can comprise a deglycosylated autologous tumor cells or tumor cell lysate as described above, wherein the tumor cells or tumor cell lysate is combined with at least one additional component selected from the group consisting of pharmaceutically-acceptable carriers, adjuvants, diluents, preservatives, antibiotics, and combinations thereof prior to administration. A "pharmaceutically-acceptable carrier" refers to includes any and all solvents, dispersion media, coatings, stabilizing agents, diluents, preservatives, antibacterial and antifungal agents, isotonic agents, adsorption delaying agents, and the like. Diluents can include water, saline, dextrose, ethanol, glycerol, and the like. Isotonic agents can include sodium chloride, dextrose, mannitol, sorbitol, and lactose, among others. Stabilizers include albumin and alkali salts of ethylendiamintetracetic acid, among others.

Adjuvants are as described above.

A "protectant" or "preservative" as used herein, refers to an anti-microbiological active agent, such as for example Neomycin, Amphoteracin B, Gentamycin, Merthiolate, and the like. Of these, Neomycin and/or Amphoteracin B are particularly preferred. In particular adding a protectant is most preferred for the preparation of a multi-dose composition. Those anti-microbiological active agents are added in concentrations effective to prevent the composition of interest from any microbiological contamination or for inhibition of any microbiological growth within the composition of interest.

Moreover, this method can also comprise the addition of any stabilizing agent, such as for example saccharides, trehalose, mannitol, saccharose and the like, to increase and/or maintain product shelf-life.

Thus, the composition of the present disclosure can comprise a deglycosylated tumor cell lysate, together with a dispersion media, or a solvent, or a coating, or a stabilizing agent, or a diluent, or a preservative, or an adjuvant, or an antibacterial or antifungal agent, or an isotonic agent, or an adsorption delaying agent, or any combination of the above.

In additional preferred forms, the composition of the present disclosure can comprise deglycosylated autologous tumor cells or deglycosylated tumor cell lysate derived from allogeneic cancer cells. In one embodiment, allogeneic cancer cells may be sourced from another member of the same species as the patient. In another embodiment, allogeneic cancer cells may be sourced from another the same tumor type. Non-limiting sources of allogeneic cancer cells comprise of laboratory-grown cancer cell lines and tumor cells isolated from a donor. In certain embodiments, allogeneic tumor cells may be genetically modified.

The composition of the present disclosure may comprise a deglycosylated tumor vaccine derived from deglycosylated allogeneic cancer cells to be used as a cancer prevention vaccine. As used herein, a "cancer prevention vaccine" is administered to healthy patients to prevent cancers from developing. In one embodiment, the deglycosylated cancer cell cancer prevention vaccine may be derived of cancer cells from multiple cancer types. In another embodiment, the deglycosylated cancer cell cancer prevention vaccine may be derived of cancer cells from one or more cancer types. In yet another embodiment, the deglycosylated cancer cell cancer prevention vaccine may be derived of cancer cells from at least five, at least four, at least three, at least two, at least one cancer types. In one embodiment, the deglycosylated cancer cell cancer prevention vaccine may be administered to the patient multiple times over an appropriate time span to achieve the desired response. In certain embodiments, the deglycosylated cancer cell cancer prevention vaccine may be administered to the patient at least 10 times, at least 9 times, at least 8 times, at least 7 times, at least 6 times, at least 5 times, at least 4 times, at least 3 times, at least 2 times, at least once. In another embodiment, the deglycosylated cancer cell cancer prevention vaccine may be administered to the patient at appropriate time intervals. In certain embodiments, the deglycosylated cancer cell cancer prevention vaccine may be administered to the patient at least every 5 years, at least every 3 years, at least every year, at least every 9 months, at least every 6 months, at least every 3 months, at least every month, at least every 3 weeks, at least every 2 weeks, at least every week, at least every four days, at least every two days, at least every day.

DRAWINGS

The drawings described herein are for illustration purposes only and are not intended to limit the scope of the present teachings in any way.

Corresponding reference numerals indicate corresponding parts throughout the several views of drawings.

DETAILED DESCRIPTION

Figure 1:
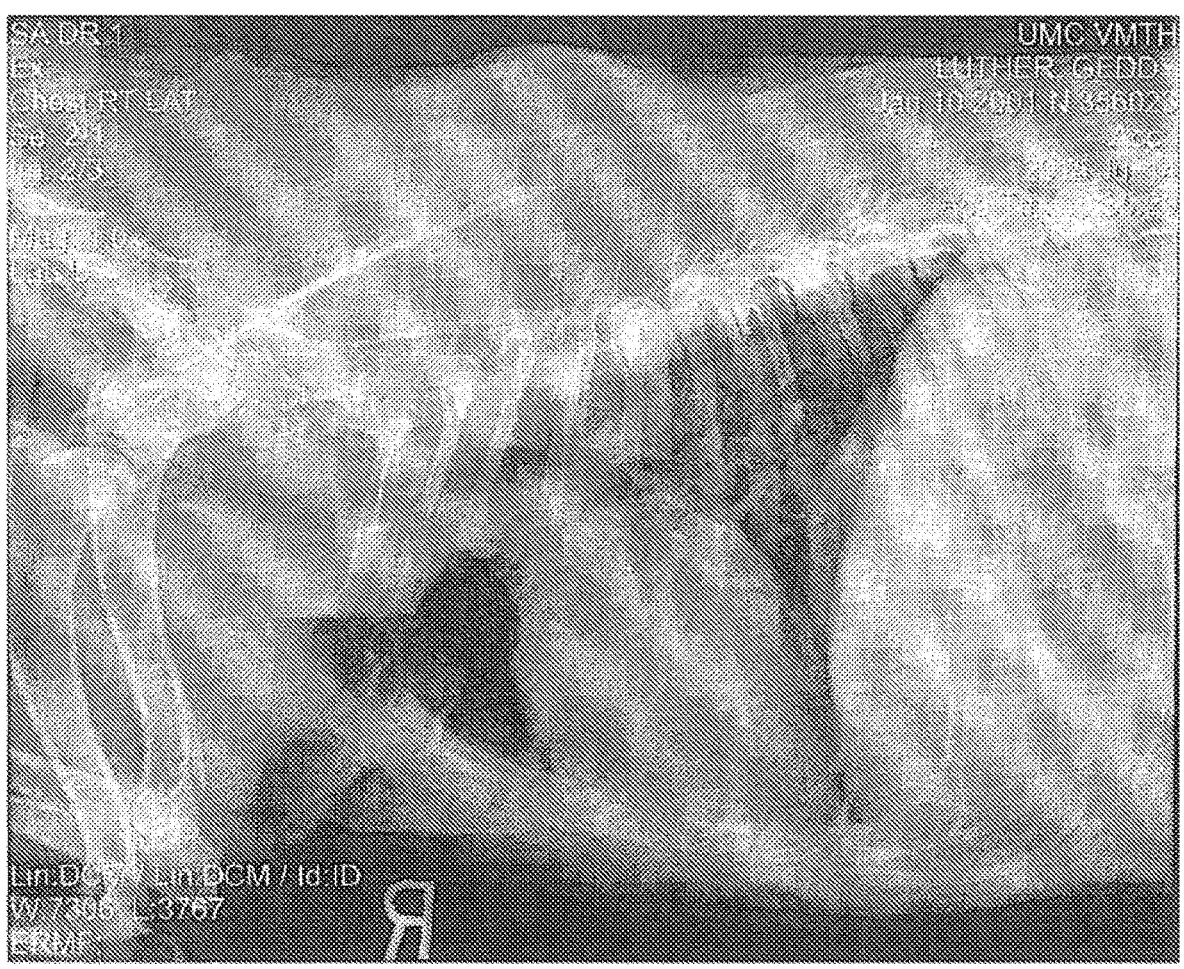
FIG. 1 is an x-ray showing metastatic nodule identified throughout the lung fields.

The following description is merely exemplary in nature and is in no way intended to limit the present teachings, application, of uses. Throughout this specification, like reference numerals will be used to refer to like elements.

The disclosure teaches a novel therapeutic vaccine approach that can trigger a therapeutic antitumor response in a cancer patient or a healthy subject. The inventive approach is to selectively eliminate the carbohydrate sequences from tumor cells without affecting the tumor associated protein epitopes. The disclosure further teaches that the evidence that in humans, the expression of Lewis$^y$, SLEX and other carbohydrate sequences increases dramatically on tumor cells near the end stage of cancer, suggests that these TACAs help to make them invulnerable to the immune response. Thus the loss of these TACAs will de-shield these tumor cells from companion dogs, revealing immunogenic molecules that will trigger a therapeutic antitumor response.

More specifically, the disclosure teaches that first, a suitable method may have to be generated to isolate tumor cells from other normal cells within the tumor. There are numerous ways to perform this type of isolation, which will likely be specific for the type of cancer cells that are targets. Once such tumor cells are isolated, it may be important first to shut down protein synthesis with an active DNA cross-linking agent like mitomycin C. An active inhibitor of glycosylation may also be necessary to globally eliminate the additional of any more glycan sequences. The famous AIDS drug AZT is an excellent inhibitor of glycosylation at a final concentration of about 20 µM. These two drugs can be given to the tumor cells, which may be incubated with a variety of different glycosidases (neuraminidase, β-galactosidase, (β- and α-N-acetylgalactosaminidase, α-fucosidase, α-mannosidase, and endo-β-galactosidase). These enzymes may be able to extensively digest the surface glycans on the tumor cells, enabling immune cell access to tumor associated epitopes that are newly exposed and for which tolerance has not been induced. The digested tumor cells may be collected and screened for the loss of specific glycan epitopes with antibodies and lectins to confirm their removal. Once deglycosylated on is achieved, cells may be injected intramuscularly or into the peritoneal cavity of cancer patients along with alum and monophoryl lipid A adjuvants.

The inventor has initiated a prospective, single arm efficacy trial of an adjuvanted deglycosylated tumor vaccine in canines. Tumor specimens (about 3 cm$^3$) were collected surgically during treatment of naive dogs that had developed either melanoma or apocrine gland anal sac adenocarcinoma (AGASACA). In some cases, draining lymph nodes were not removed to determine the efficacy of immune activation. Tumor cells were isolated and treated with exoglycosidases and chemical oxidation procedures to remove CFGs. Successful elimination of CFGs was confirmed by lectin binding analysis of the treated cells. The tumor cells were subjected to 5× freeze-thaw cycles to kill them and generate tumor cell lysates. This lysate was mixed with AS04 adjuvant (alum, monophosphoryl lipid A) in physiological saline (0.14 M). This combination is routinely employed in vaccinations against viruses and bacteria in humans. Dogs were inoculated subcutaneously at different sites on their limbs with lysates from 7-10×10$^6$ cells at 0, 2, 4 and 6 weeks.

The following examples are included to demonstrate preferred embodiments of the disclosure. It should be appreciated by those of skill in the art that the techniques disclosed in the examples that follow represent techniques discovered by the inventors to function well in the practice of the disclosure, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

Example 1. Vaccine Immunization Therapy on a Dog with Cancer

The mass in the patient dog, a 14 year old neutered male cocker spaniel, was identified in the mouth in addition to multiple metastatic lymph nodes. A 2.5 cm$^3$ metastatic lymph node was surgically removed and confirmed as a melanoma. Initial thoracic radiographs were unremarkable. The mass was surgically removed again and tumor cells were isolated and expanded in culture using standard methods. Tumor cells were deglycoslated as described herein. Lysates of deglycoslated tumor cells were prepared and mixed with an AS04 adjuvant system for preparation of autologous vaccine. The patient dog was vaccinated with the resulting autologous vaccine four times at 2 week intervals (0, 2, 4, and 6 weeks). Each inoculation was performed intradermally over the right popliteal region. Each dose contained lysates from 7 million deglycoslated tumor cells and 550 mg of AS04 suspended in 0.5 ml of physiological saline.

Refer to FIG. 1. Radiographs of the thorax on before first surgical intervention revealed the development of metastatic disease in the lung fields.

Figure 2:
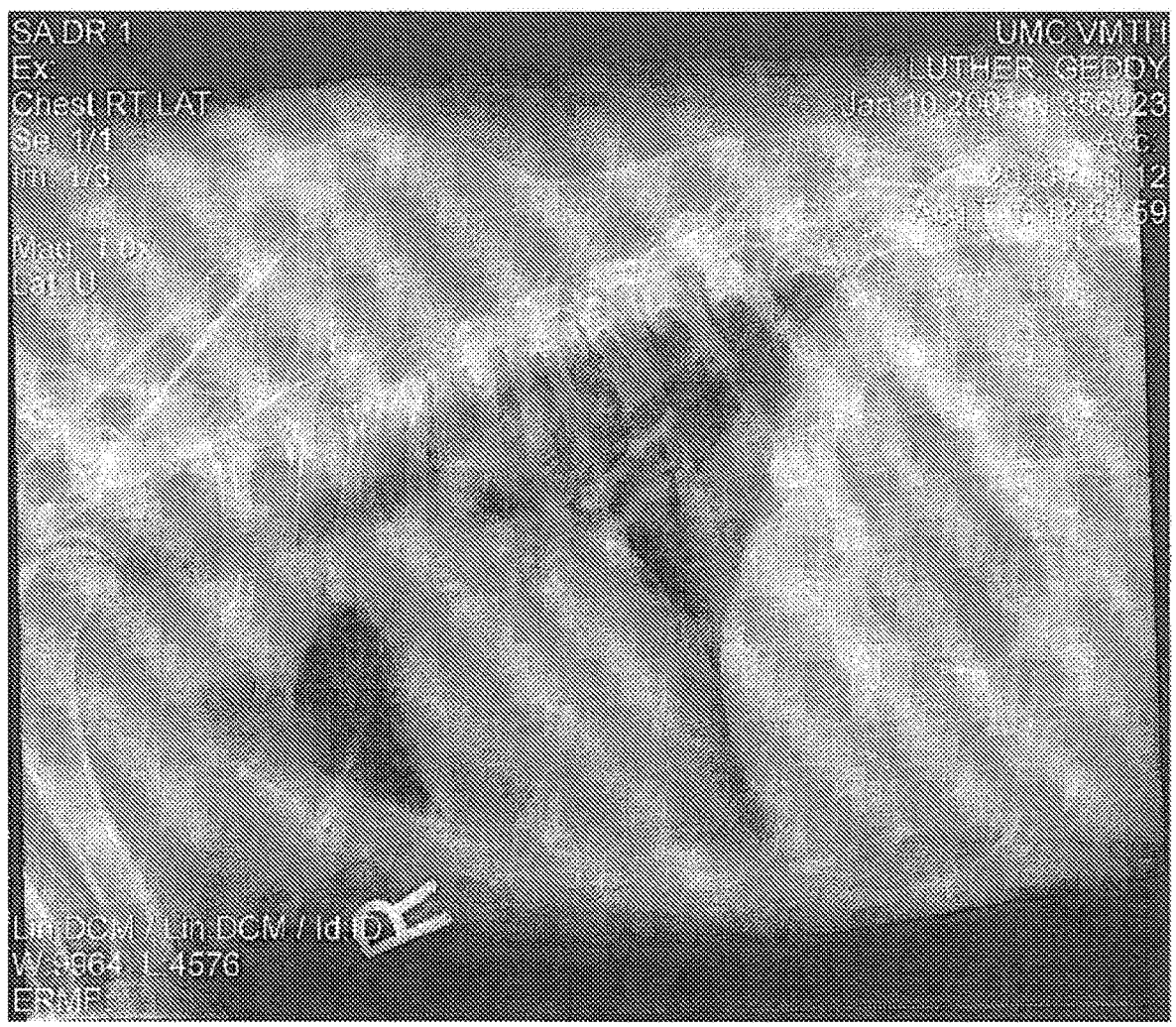
FIG. 2 is an x-ray showing the metastatic nodules identified in FIG. 1 had progressed.

Refer to FIG. 2. Radiographs of the thorax on before surgical harvest of the metastatic lymph node revealed progression of metastatic disease.

Figure 3:
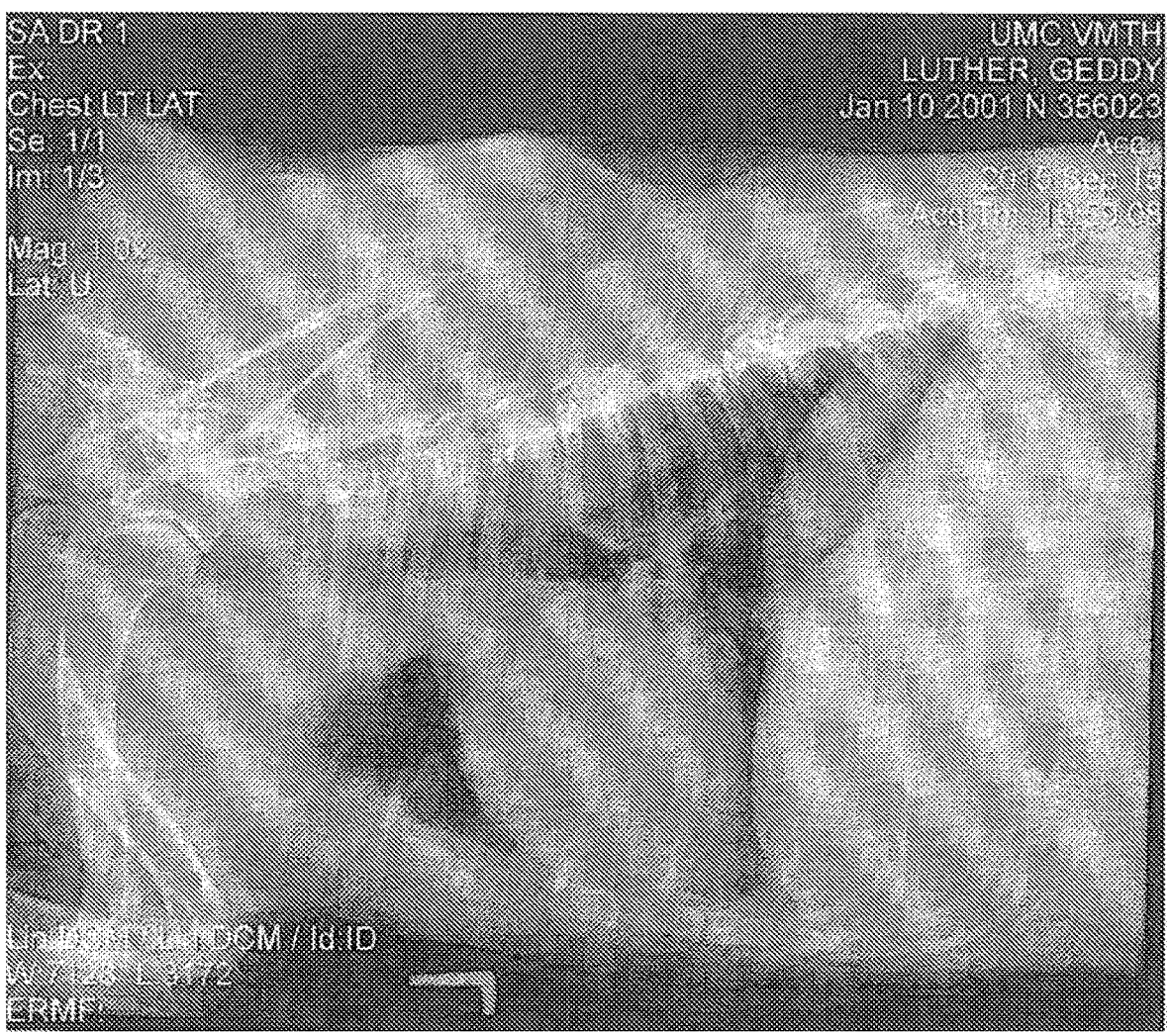
FIG. 3 is an x-ray showing no metastatic disease clearly visible after treatment.

Refer to FIG. 3. Radiographs of the thorax after the fourth inoculation revealed resolution of metastatic disease. No other therapy was administered to this dog.

Example 2. Preparation of an Adjuvanted, Deglycosylated Autologous Tumor Vaccine from Canine Tumor Cells Melanoma or AGASACA tumors or metastatic nodes (about 3-4 cm$^3$) were surgically excised from the canine patient and placed in a sterile tube containing chilled RPMI 1640 media (Gibco) on ice and immediately transferred to a tissue culture suite. Tumor cells were separated from non-tumor cell types (e.g., blood cells, fibroblasts, supportive cell types) and connective tissues using the Miltenyi Biotec tumor dissociation kit (for human tumor cells) in conjunction with a gentleMACS Dissociator. The resulting dissociated tumor cells were plated out in RPMI 1640 media (Gibco) containing 10% fetal calf serum (Sigma-Aldrich), 100 units of penicillin-streptomycin mixture/ml (Gibco), Glutamax (L-alanyl-L-glutamine; 1 ml/100 ml of media; Gibco) and Fungizone (amphotericin B (1 ml/500 ml)). Tumor cells were allowed to adhere to the plate, while other cells stayed in suspension. After three days, nonadherent contaminating cells were removed, leaving about 500,000-1 million tumor cells/cm$^3$ tumor tissue. These tumor cells were seeded into two T-75 flasks. The tumor cells were expanded in culture until about 35-40 million tumor cells were obtained.

To deglycosylate the tumor cells, cells were suspended in new media (2 million cells/nil) supplemented with 5 μg/multunicamycin (Sigma-Aldrich), 2 mM benzyl 2-acetamido-2-deoxy-α-D-galactopyrano side (Sigma-Aldrich) and D-threo-1-phenyl-2-decanoylamino-3-morpholino-1-propanol (Matreya LLC) to inhibit N-glycosylation, O-glycosylation and glycosphingolipid synthesis, respectively. The media was also supplemented with the following glycosidases: neuraminidase from *Clostridium perfringens* (New England BioLabs, 100 units/ml), β1-4 galactosidase from *Streptococcus pneumoniae* (Prozyme, 10 mU/ml) and endo-β-galactosidase (QA-Bio, 30 mU/ml). The tumor cells were incubated for 3 hours, centrifuged (500×g, 10 minutes), and washed with physiological saline (0.85% NaCl). They were then resuspended in 50 mM sodium phosphate buffer (pH 6.0) containing 0.15 M NaCl and freshly prepared 50 mM sodium-m-periodate. The cells were incubated for 1 hour in the dark at 23° C. Periodate oxidation was terminated by the addition of 50 (0.1.1 of ethylene glycol/ml of buffer.

Deglycosylated tumor cells were next pelleted by centrifugation (500×g, 10 minutes) resuspended in physiologic saline and transferred to a cryovial. The cells were pelleted again by centrifugation. The cells were subjected to five freeze-thaw cycles (-80° C., 37° C.) to break the cellular membrane and generate lysates.

Tumor cell lysates were mixed with 2.2 mg of Adjuvant System 04 (AS04). AS04 is a mixture of Alhydrogel® adjuvant 2% and 220 μg of synthetic monophosphoryl lipid A that induces a transient localized innate immune response that enhances adaptive immunity in humans. The lysate and AS04 were suspended in sterile physiological saline to a final volume of 2.2 ml. This vaccine was immediately refrigerated and stored at 4° C.

Example 3. Assessment of an Adjuvanted, Deglycosylated Autologous Tumor Vaccine on Metastatic Progression in Canines Four dogs with naturally-occurring oral melanoma were enrolled into a single-arm trial to assess the efficacy of an adjuvanted, deglycosylated autologous tumor vaccine. To be included in the study, dogs could be of any sex but a minimum weight of 10 kg was required. Dogs in the study had an oral melanoma lesion of at least 2 cm in longest diameter or metastatic lymph nodes that could be surgically resected for vaccine preparation. Dogs could be of any stage of disease progression, but a performance score of 0 or 1 with a minimum estimated life expectancy of 12 weeks was required for inclusion. Dogs could not be receiving immunosuppressive therapy. Metastatic lesions could not have been treated with radiation therapy. Dogs with melanoma could not have received the ONCEPT® vaccine prior to enrollment or during the trial. Prior chemotherapy was allowed with a three week washout prior to trial enrollment. Comorbidities, including kidney disease with azotemia, liver disease or hepatic enzymopathy greater than twice the upper limit of basal state, or chronic infection were not allowed.

Prior to the start of therapy, dogs were evaluated by thoracic radiographs and draining lymph node aspirate for accurate staging. Abdominal ultrasound was performed at clinician discretion to evaluate for abdominal metastasis as indicated. Dogs underwent surgery at the start of the trial to resect the tumor, with clear margins where possible. Tumor cells were isolated from a portion of the tumor and treated with exoglycosidases and chemical oxidation procedures to remove carbohydrate functional groups (CFGs). Successful elimination of CFGs was confirmed by lectin binding analysis of the treated cells. The tumor cells were subjected to five freeze-thaw cycles to kill the cells and generate tumor cell lysates. The resulting lysate was mixed with AS04 adjuvant (alum, monophosphoryl lipid A) in physiological saline. Dogs were inoculated subcutaneously at different sites on their limbs with lysates from $7-10 \times 10^6$ cells at 0, 2, 4 and 6 weeks. Prior to the first vaccine administration, and at each subsequent administration, then monthly thereafter, blood was collected for humoral and cellular assays to evaluate tumor-specific immune response. Thoracic radiographs were repeated every 2 months until 6 months, then every 3 months thereafter. Draining lymph nodes was monitored by palpation and aspiration on the same schedule as thoracic radiographs are made.

None of the treated dogs developed adverse events following vaccination. As shown in Table 1, the metastasis was resolved in three of the four dogs. Of those three dogs, the average age of survival was 447±108 days following diagnosis.

are characterized by having at least 50% of the carbohydrate functional groups thereon disrupted in comparison to a normal cancer cell from the same type of cancer as the modified cancer cell;

an adjuvant; and at least one additional component selected from the group consisting of pharmaceutically-acceptable carriers, diluents, preservatives, antibiotics, and combinations thereof, wherein said carbohydrate functional groups are disrupted by a step comprising incubation with at least one deglycosidase such that they have a decreased overall number of carbohydrate chains or where they have shorter, truncated carbohydrate chains;

and further comprising a step comprising incubation with an oxidizing agent.

2. The composition of claim 1, wherein said adjuvant is AS04.

3. The composition of claim 1, wherein the quantity of modified cancer cells is between 500,000 and 100,000,000 cells.

4. The composition of claim 1, wherein the modified cancer cells are from a solid cancer.

5. The composition of claim 1, wherein the modified cancer cells are from a liquid cancer.

6. The composition of claim 1, wherein the modified cancer cells are from a Stage I, Stage II, Stage III, or Stage 4 cancer.

7. The composition of claim 1, wherein the composition further comprises one or more chemotherapeutic compositions.

8. The composition of claim 1, wherein the modified cancer cells are all from the same individual.

9. The composition of claim 1, wherein at least 2 deglycosidases are used to disrupt said carbohydrate functional groups.

10. The composition of claim 1, wherein the at least one deglycosidase is selected from the group consisting of exoglycosidases, endoglycosidases, and any combination thereof.

| Dog | Diagnosis | Date of Diagnosis | Node Metastasis | Distant Metastasis | Stage of Diagnosis | Outcome of Metastases | Date of Death | Survival |
|---|---|---|---|---|---|---|---|---|
| 1 | Caudal Mandible Melanoma | Aug. 5, 2014 | + Aug. 5, 2014 | + Sep. 11, 2014 | IV | Progressive | Oct. 15, 2014 | 71 |
| 2 | Left Mandible Amelanotic Melanoma | Apr. 27, 2015 | + May 1, 2015 | + Aug. 12, 2015 | II progressed to IV | Resolved | Feb. 4, 2017 | 646 |
| 3 | Left Cervical Lymph Node Metastatic Melanoma | Dec. 15, 2015 | + Dec. 15, 2015 | – | III | Resolved | Alive | 423 |
| 4 | Right Maxillary Melanoma | May 23, 2016 | – | – | II | None | Alive | 273 |

The description herein is merely exemplary in nature and, thus, variations that do not depart from the gist of that which is described are intended to be within the scope of the teachings. Such variations are not to be regarded as a departure from the spirit and scope of the teachings.

What is claimed is:

1. A composition comprising: a cancer cell lysate, wherein the cancer cell lysate comprises modified cancer cells that 11. The composition of claim 10, wherein the at least one deglycosidase is selected from the group consisting of neuraminidase, β-galactosidase, β- and α-N-acetylgalactosaminidase, α-fucosidase, α-mannosidase, endo-β-galactosidase, neuraminidase, and any combination thereof.

12. A composition comprising: a cancer cell lysate, wherein the cancer cell lysate comprises between 500,000 and 100,000,000 modified cancer cells that are characterized by having at least 50% of the carbohydrate functional groups thereon disrupted in comparison to a normal cancer cell from the same type of cancer as the modified cancer cell;
an adjuvant; and
at least one additional component selected from the group consisting of pharmaceutically-acceptable carriers, diluents, preservatives, antibiotics, and combinations thereof,
wherein said carbohydrate functional groups are disrupted by a step comprising incubation with at least one deglycosidase such that they have a decreased overall number of carbohydrate chains or where they have shorter, truncated carbohydrate chains.

13. A method of treating cancer in a patient comprising the steps of:
obtaining a sample of cancer cells from the same type of cancer as the patient;
subjecting said cancer cells to a deglycosylating process using at least one deglycosidase and an oxidizing agent wherein the cancer cells have at least 50% of the carbohydrate functional groups thereon disrupted in comparison to a normal cancer cell from the same type of cancer that has not been subjected to a deglycosylating process, thereby resulting in deglycosylated cancer cells;
lysing said deglycosylated cancer cells;
producing a cancer cell lysate from said lysed deglycosylated cancer cells; and
administering said cancer cell lysate to the patient,
wherein said carbohydrate functional groups are disrupted by a step comprising incubation with said at least one deglycosidase such that they have a decreased overall number of carbohydrate chains or where they have shorter, truncated carbohydrate chains; and
subjecting the deglycosylated cancer cells to a step comprising incubation with an oxidizing agent.

14. The method of claim 13, wherein the cancer cell lysate is combined with at least one additional component selected from the group consisting of pharmaceutically-acceptable carriers, adjuvants, diluents, preservatives, antibiotics, and combinations thereof prior to administration to the patient.

15. The method of claim 14, wherein said at least one additional component is an adjuvant.

16. The method of claim 15, wherein said adjuvant is AS04.

17. The method of claim 13, wherein the sample of cancer cells comprises between 500,000 and 100,000,000 cancer cells.

18. The method of claim 13, wherein said lysing is performed through a series of freeze/thaw cycles.

19. The method of claim 13, wherein the deglycosylating process comprises incubating said cancer cells with at least one deglycosylating agent.

20. The method of claim 13, further comprising the step of administering a different cancer therapy or treatment.

21. The method of claim 13, wherein said administering step comprises intradermal administration.

22. The method of claim 13, wherein said administering to the patient results at least one outcome selected from the group consisting of tumor growth impairment of at least 5%, tumors shrinking at least 5%, at least a 5% reduction in the incidence of tumor markers, at least a 5% increase in life expectancy, and combinations thereof, wherein the outcome is in comparison to a patient with an identical disease condition that did not receive an administration of said cancer cell lysate and wherein the tumor is a melanoma or an apocrine gland sac carcinoma.

23. The method of claim 13, wherein at least 2 deglycosidases are used to disrupt said carbohydrate functional groups.

24. The method of claim 13, wherein the at least one deglycosidase is selected from the group consisting of exoglycosidases, endoglycosidases, and any combination thereof.

25. The method of claim 24, wherein the at least one deglycosidase is selected from the group consisting of neuraminidase, β-galactosidase, β- and α-N-acetylgalactosaminidase, α-fucosidase, α-mannosidase, endo-β-galactosidase, neuraminidase, and any combination thereof.

* * * * *